(12) United States Patent
Yang et al.

(10) Patent No.: US 10,682,421 B2
(45) Date of Patent: Jun. 16, 2020

(54) NANOPARTICLE COMPOSITION FOR USE IN TARGETING CANCER STEM CELLS AND METHOD FOR TREATMENT OF CANCER

(71) Applicant: City University of Hong Kong, Hong Kong (HK)

(72) Inventors: Mengsu Yang, Hong Kong (HK); Dandan Liu, Baoding (CN)

(73) Assignee: CITY UNIVERSITY OF HONG KONG, Kowloon Tong (HK)

( * ) Notice: Subject to any disclaimer, the term of this patent is extended or adjusted under 35 U.S.C. 154(b) by 0 days.

(21) Appl. No.: 15/915,166

(22) Filed: Mar. 8, 2018

(65) Prior Publication Data
US 2018/0193485 A1 Jul. 12, 2018

Related U.S. Application Data

(63) Continuation-in-part of application No. 14/745,639, filed on Jun. 22, 2015, now abandoned.

(51) Int. Cl.
| | | |
|---|---|---|
| *A61K 47/69* | (2017.01) | |
| *A61K 41/00* | (2020.01) | |
| *A61K 49/00* | (2006.01) | |
| *A61K 47/68* | (2017.01) | |
| *C07K 16/30* | (2006.01) | |
| *A61K 39/395* | (2006.01) | |
| *A61N 2/00* | (2006.01) | |
| *A61P 35/00* | (2006.01) | |
| *A61K 9/00* | (2006.01) | |
| *C07K 16/28* | (2006.01) | |
| *A61K 39/00* | (2006.01) | |

(52) U.S. Cl.
CPC ........ *A61K 47/6925* (2017.08); *A61K 9/0019* (2013.01); *A61K 39/3955* (2013.01); *A61K 39/39558* (2013.01); *A61K 41/0052* (2013.01); *A61K 47/6849* (2017.08); *A61K 47/6923* (2017.08); *A61K 47/6929* (2017.08); *A61K 49/0019* (2013.01); *A61K 49/0045* (2013.01); *A61K 49/0058* (2013.01); *A61K 49/0093* (2013.01); *A61N 2/002* (2013.01); *A61P 35/00* (2018.01); *C07K 16/30* (2013.01); *A61K 2039/505* (2013.01); *A61K 2039/54* (2013.01); *A61K 2039/545* (2013.01); *C07K 16/2887* (2013.01)

(58) Field of Classification Search
None
See application file for complete search history.

(56) References Cited

U.S. PATENT DOCUMENTS 6,514,481 B1 2/2003 Prasad et al.
2010/0303716 A1 12/2010 Jin et al.
2012/0022026 A1 1/2012 Krawczyk et al.
2012/0269721 A1 10/2012 Weng et al.
2016/0367671 A1 12/2016 Yang et al.

OTHER PUBLICATIONS

Reya et al., "Stem Cells, Cancer, and Cancer Stem Cells", Insight Review Articles, vol. 414, Nov. 2001, 7 pages.
Connie Eaves, "Here, There, Everywhere", Cancer Stem Cells, vol. 456/4, Dec. 2008, 2 pages.
Chen et al., "Understanding and Targeting Cancer Stem Cells; Therapeutic Implications and Challenges", Acta Pharmacologica Sinica (2013) 34: 732-740.
Desai et al., Alveolar Progenitor and Stem Cells in Lung Development, Renewal and Cancer, Nature, vol. 507, Mar. 13, 2014, 16 pages.
Akunuru et al., Non-small Cell Lung Cancer Stem/Progenitor Cells are Enriched in Multiple Distinct Phenotypic Subpopulations and Exhibit Plasticity, Cell Death and Disease (2012) 3, e352, 10 pages.
Zhang et al., "Stemness and Inducing Differentiation of Small Cell Lung Cancer NCI-H446 Cells", Cell Death and Disease (2013) 4, e633, 13 pages.
Domingo-Domenech et al.,"Suppression of Acquired Docetaxel Resistance in Prostate Cancer Through Depletion of Notch-and Hedgehog-Dependent Tumor-Initiating Cells", Cancer Cell 22, Sep. 11, 2012, 373-388.
Burke et al., "Targeting Cancer Stem Cells with Nanoparticle-Enabled Therapies", Molecular Biomarkers & Diagnosis, 2012, S8:003, 4 pages.
Wang et al., "Involvement of ROS in the Inhibitory Effect of Thermotherapy Combined with Chemotherapy on A549 Human Lung Adenocarcinoma Cell Growth Through the AKT Pathway", Oncology Reports 28, 2012, 1369-1375.

(Continued)

*Primary Examiner* — Michael G. Hartley
*Assistant Examiner* — Lance W Rider
(74) *Attorney, Agent, or Firm* — Melvin Li; Heslin Rothenberg Farley & Mesiti PC

(57) ABSTRACT

There is disclosed a composition in the form of a nanoparticle. The nanoparticle composition has a diameter from 5 to 500 nanometers. The nanoparticle composition has i) a central core portion including magnetic $Fe_3O_4$ nanoparticles adapted to act as a heat source when subjected to a magnetic field and a chemotherapeutic agent configured to treat cancer tissues, ii)—a shell portion including a shell member encapsulating said core portion, and iii)—antibodies configured to target cancer stem cells and adhered to surface of said shell member. The chemotherapeutic agent is a heat shock protein inhibitor and is releasable on activation of the heat source due to the magnetic field, and the shell member is made of silica or a silica based material. Surface of the nanoparticle is modified with the antibodies capable of binding with a cluster of differentiation molecules on the cell surface of the target cancer stem cells, whereby by way of combination of specificity of the nanoparticle composition due to the antibody, thermo-therapeutic effect of the $Fe_3O_4$ nanoparticles, and release of the heat shock protein inhibitor on site at the target cancer stem cells, inhibition of the target cancer stem cells is synergistically and additionally enhanced is increased.

10 Claims, 27 Drawing Sheets

(27 of 27 Drawing Sheet(s) Filed in Color)

(56) References Cited

OTHER PUBLICATIONS

Beug et al., "Smac Mimetics and Innate Immune Stimuli Synergize to Pomote Tumor Death", Nature Biotechnology, vol. 32, No. 2, Feb. 2014, 12 pages.

Shyh-Dar Li et al., "Tumor-Targeted Delivery of siRNA by Self-Assembled Nanoparticles", NIH Public Access, Mol Ther., Jan. 2008: 16(1): 163-169, 17 pages.

Haiyan Chen et al., "Multifunctional Gold Nanostar Conjugates for Tumor Imaging and Combined Photothermal and Chemo-therapy", Theranostics 2013, vol. 3, Issue 9, 633-649.

Feifei Li et al., "Molecular-targeted Agents Combination Therapy for Cancer Developments and Potentials", International Journal of Cancer, 134, 2014, 1257-1269.

Mark E. Davis et al., Nanoparticle Therapeutics: An Emerging Treatment Modality for Cancer, Nature Reviews Drug Discovery, vol. 7, Sep. 2008, 12 pages.

Mamaeva et al., Mesoporous Silica Nanoparticles as Drug Delivery Systems for Targeted Inhibition of Notch Signaling in Cancer, The American Society of Gene & Cell Therapy, www.moleculartherapy.org, vol. 19, No. 8, Aug. 2011, 1538-1546.

Yong Wang et al., Co-Delivery of Drugs and DNA from Cationic Core-Shell Nanoparticles Self-Assembled From a Biodegradable Copolymer, Nature Materials, vol. 5, Oct. 2006, 791-796.

Sun et al., "Co-Delivery of pEGFP-hTRAIL and Paclitaxel to Brain Glioma Mediated by an Angiopep-Conjugated Liposome", Biomaterials 33 (2012), 916-924.

Meng et al., "Co-Delivery of an Optimal Drug/siRNA Combination Using Mesoporous Silica Nanoparticle to Overcome Drug Resistance in Breast Cancer In Vitro and In Vivo", ACS Nano, Feb. 26, 2013; 7(2): 994-1005.

Dandan Liu et al., "Reorganization of Cytoskeleton and Transient Activation of Ca2+ Channels in Mesenchymal Stem Cells Cultured on Silicon Nanowire Arrays", Applied Materials & Interfaces, 2013, 13295-13304.

Dandan Liu et al., "Activation of Multiple Signaling Pathways During the Differentiation of Mesenchymal Stem Cells Cultured in a Silicon Nanowire Microenvironment", Nanomedicine: Nanotechnology, Biology and Medicine 10 (2014) 1153-1163.

Craig T. Jordan, "Cancer Stem Cells: Controversial or Just Misunderstood?", Cell Stem Cell. Mar. 6, 2009: 4(3): 5 q pages.

Mamiya et al., "Hyperthermic Effects of Dissipative Structures of Magnetic Nanoparticles in Large Alternating Magnetic Fields", Scientific Reports 1:157, 2011, 7 pages.

Takeshi Kobayashi, "Cancer Hyperthermia Using Magnetic Nanoparticles", Biotechnology Journal, 2011, 6, q 1342-1347.

Workman et al., Chaperoning Cell Death: A Critical Dual Role for Hsp90 in Small-Cell Lung Cancer, Nature Chemical Biology vol. 3 No. 8, Aug. 2007, 3 pages.

Gao et al., "Ligand Modified Nanoparticles Increases Cell Uptake, Alters Endocytosis and Elevates Glioma Distribution and Internalization", Scientific Reports 3:2534, 2013, 8 pages.

Mickler et al., "Tuning Nanoparticle Uptake: Live-Cell Imaging Reveals Two Distinct Endocytosis Mechanisms Mediated by Natural and Artificial EGFR Targeting Ligand", Nano Letters, 2012, 12, 3417-3423.

McMahon et al., "Molecular Mechanisms and Physiological Functions of Clathrin-Mediated Endocytosis", Nature Reviews, Molecular Cell Biology, vol. 12, Aug. 2011, 17 pages.

Vuong et al., "Preubiquitinated Chimeric ErbB2 is Constitutively Endocytosed and Subsequently Degraded in Lyosomes" SciVerse ScienceDirect, Experimental Cell Research 319 (2013) 32-45.

Bertelsen et al., A Chimeric Pre-Ubiquitinated EGF Receptor is Constitutively Endocytosed in a Clathrin-Dependent, but Kinase-Independent Manner, Traffic 2011; 12: 507-520.

Weissleder et al., "Cell-Specific Targeting of Nanoparticles by Multivalent Attachment of Small Molecules", Articles Nature Biotechnology, vol. 23, No. 11, Nov. 2005, 1418-1423.

Liong et al., Multifunctional Inorganic Nanoparticles for Imaging, Targeting, and Drug Delivery, ACS Nano. May 2008, 2(5): 889-896.

Lee et al., "Exchange-Coupled Magnetic Nanoparticles for Efficient Heat Induction", Nature Nanotechnology, www.nature.com/naturenanotechnology, 2011, 15 pages.

Davis et al., "Therapy of B-Cell Lymphoma with Anti-CD20 Antibodies Can Result in the Loss of CD20 Antigen Expression", Clinical Cancer Research, vol. 5, Mar. 2009, 611-615.

Kvinlaug, B.T., et al., "Targeting cancer stem cells", Expert Opinion on Therapeutic Targets, 2007, pp. 915-927.

Advisory Action in U.S. Appl. No. 14/745,639, filed on Mar. 13, 2018.

Final Office Action in U.S. Appl. No. 14/745,639, filed on Jan. 11, 2018.

Office Action in U.S. Appl. No. 14/745,639, filed on Jun. 1, 2017.

Restriction Requirement in U.S. Appl. No. 14/745,639, filed on Apr. 19, 2017.

Biffi, S., et al., "In Vivo Biodistribution and Lifetime Analysis of Cy5.5-Conjugated Rituximab in Mice Bearing Lymphoid Tumor Xenograft Using Time-Domain Near-Infrared Optical Imaging", Molecular Imaging, 2008, pp. 272-282 (Year: 2008).

V Schlaak, M., et al., "Regression of metastatic melanoma by targeting cancer stem cells", Oncotarget, 2012, pp. 22-30 (Year: 2012).

Office Action in U.S. Appl. No. 14/745,639, filed on Jun. 26, 2018, 43 pgs.

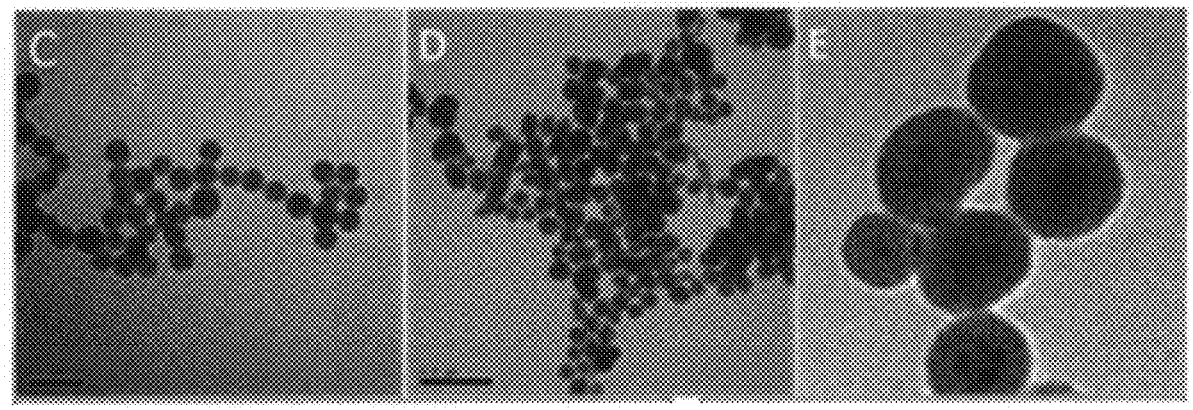
FIG. 1C　　　　FIG. 1D　　　　FIG. 1E
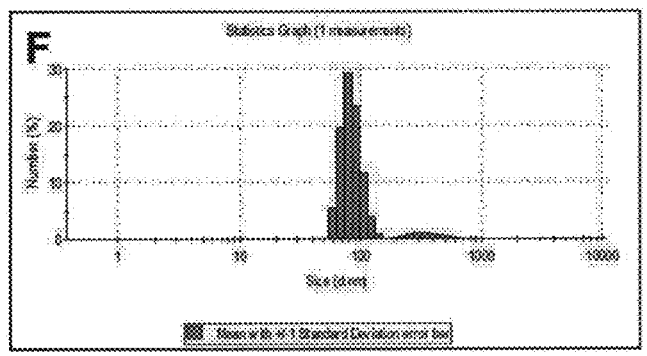
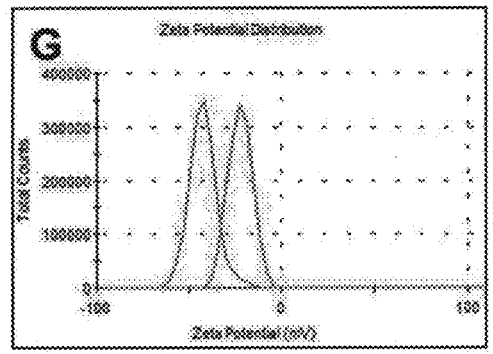
FIG. 1F　　　　FIG. 1G

NANOPARTICLE COMPOSITION FOR USE IN TARGETING CANCER STEM CELLS AND METHOD FOR TREATMENT OF CANCER

FIELD OF THE INVENTION

The present invention is concerned with a nanoparticle composition for treating cancers and a method for treatment of cancer by way of targeting cancer stem cells.

BACKGROUND OF THE INVENTION

Different approaches have been proposed to treat different types of cancers. There have been proposals to treat cancers by way of specially targeting cancer cells. However, targeting cancer cells superficially has been a challenge because it is generally difficult to effect such treatment with high specifically. If a proposed treatment approach cannot effectively target cells in issue, the efficacy of the treatment would be impaired, and worse yet, the treatment would cause undesirable side effects.

The present invention seeks to address the above problems, or at least to provide a useful alternative to the public.

SUMMARY OF THE INVENTION

According to a first aspect of the present invention, there is provided a composition in the form of a nanoparticle with a diameter from 5 to 50 nanometers comprising:
  a central core portion including magnetic $Fe_3O_4$ nanoparticles adapted to act as a heat source when subjected to a magnetic field and a chemotherapeutic agent configured to treat cancer tissues,
  a shell portion including a shell member encapsulating the core portion, and
  antibodies configured to target cancer stem cells and adhered to surface of the shell member,
wherein the chemotherapeutic agent is a heat shock protein inhibitor and is releasable on activation of the heat source due to the magnetic field, and the shell member is made of silica or a silica based material, and
wherein surface of the nanoparticle is modified with the antibodies capable of binding with a cluster of differentiation molecules on the cell surface of the target cancer stem cells, whereby by way of combination of specificity of the nanoparticle composition due to the antibody, thermo-therapeutic effect of the $Fe_3O_4$ nanoparticles, and release of the heat shock protein inhibitor on site at the target cancer stem cells, inhibition of the target cancer stem cells is synergistically and additionally enhanced is increased.

Preferably, the nanoparticle composition may comprise fluorescent dyes attached to the antibodies for in vivo localization. The antibodies may be anti-CD 20 antibodies.

The shell member may have a thickness from 10 to 100 nanometers.

The magnetic nanoparticles may have a diameter or width from 1 to 50 nanometers.

The magnetic nanoparticles may be magnetically responsive, and may be super-paramagnetic nanoparticles.

The magnetic nanoparticles may be configured to be responsive to alternating magnetic field.

The antibodies may be coated on outwardly facing surface of the shell member.

According to a second aspect of the present invention, there is provided a method of treatment of cancer by way of targeting cancer stem cells, comprising administering a nanoparticle composition as described above.

Preferably, the method may comprise a step of forming a complex of the composition and the target cancer stem cells.

The method may comprise a step of exposing a target site in which the cancer cells reside to an energy source for effecting elevation of temperature of the magnetic nanoparticles, and release of the chemotherapeutic agent from the shell portion for destroying the cancer cells of the composition-cancer cell complex in the target site, wherein the energy source is an alternating magnetic field whereby extent of elevation of temperature and release of the chemotherapeutic agent is controllable by the alternating magnetic field.

The method may comprise a step of elevating temperature of the target site to 40° C. to 52° C.

The method may comprise a step of administering said nanoparticle composition intravenously, or at a dose of 10 mg to 500 mg of said nanoparticle composition intravenously per kg of body weight.

The method may comprise the administration of the nanoparticle composition once a week.

According to a third aspect of present invention, there is provided a use of a composition as described for treatment of cancer.

BRIEF DESCRIPTION OF DRAWINGS

This patent or application file contains at least one drawing executed in color. Copies of this patent or patent application publication with color drawing(s) will be provided by the Office upon request and payment of necessary fee.

Some embodiments of the present invention will now be explained, with reference to the accompanied drawings, in which:—

FIGS. 1C, 1D and 1E are transmission electron microscopic (TEM) images showing $Fe_3O_4$@SiNPs, CD20-$Fe_3O_4$@SiNPs, and CD20-$Fe_3O_4$@SiNPs, respectively;

FIG. 1F is a graph showing size distribution of the CD20-$Fe_3O_4$@SiNP by dynamic light scattering (DLS);

FIG. 1G is graph showing zeta potential of the $Fe_3O_4$@SiNPs (green) and CD20-$Fe_3O_4$@SiNPs (red);

FIGS. 6A, 6B, 6C, and 6D are graphs and images showing in vivo simultaneous thermotherapy and chemotherapy targeting LCSCs in which FIG. 6A shows relative tumor volumes of different groups of mice (8 mice in each group) under different treatment conditions; FIG. 6B shows survival rates of different groups of mice (8 mice in each group) under different treatment conditions; FIG. 6C shows relative tumor volumes of different groups of mice (8 mice in each group) under different treatment conditions; and FIG. 6D shows representative tumor sizes from of different groups of mice after different treatment conditions;

DETAILED DESCRIPTION OF PREFERRED EMBODIMENTS OF THE INVENTION

The present invention is concerned with means and methods for treatment of cancers by way of targeting cancer stem cells (CSCs) via simultaneous chemotherapy and thermotherapy synergistically.

In one specific embodiment, the means includes making use of silica-based nanoparticles with an average particle size ranging between 5 and 50 nanometers, encapsulating magnetic cores and chemotherapeutic agent, and coated with specific antibodies against surface markers of cancer cells and in particular CSCs in tumor tissues. The use of a CSC-targeted therapeutic strategy is to disrupt the maintenance and survival of CSCs. The use of a nanoparticle-based combinatorial thermotherapy and chemotherapy in the present invention is a novel therapeutic that, as shown below, demonstrates significant promise in cancer treatment. Targeting the CSCs is particularly desirable because it can disrupt tumor initiating, relapse, and metastasis. The targeting is further enhanced by way of heating and delivering drug to tumor site for treatment of the tumor tissues without damaging the surrounding normal tissues.

On main aspect of the present invention is concerned with a nanoparticle composition comprising a central core with magnetic nanoparticles acting as a heatable source, a relatively stable and biocompatible silica shell for containing a desired or effective chemotherapeutic agent and also to provide a surface for modifying characteristic of the nanoparticle, and an antibody adapted to target cancer stem cells in issue. The following illustrates the present invention by way of materials and methods used in experiments.

Materials and Methods

In Vitro Analysis of HSPI Release from Fe$_3$O$_4$@SiNPs

Figure 1A:
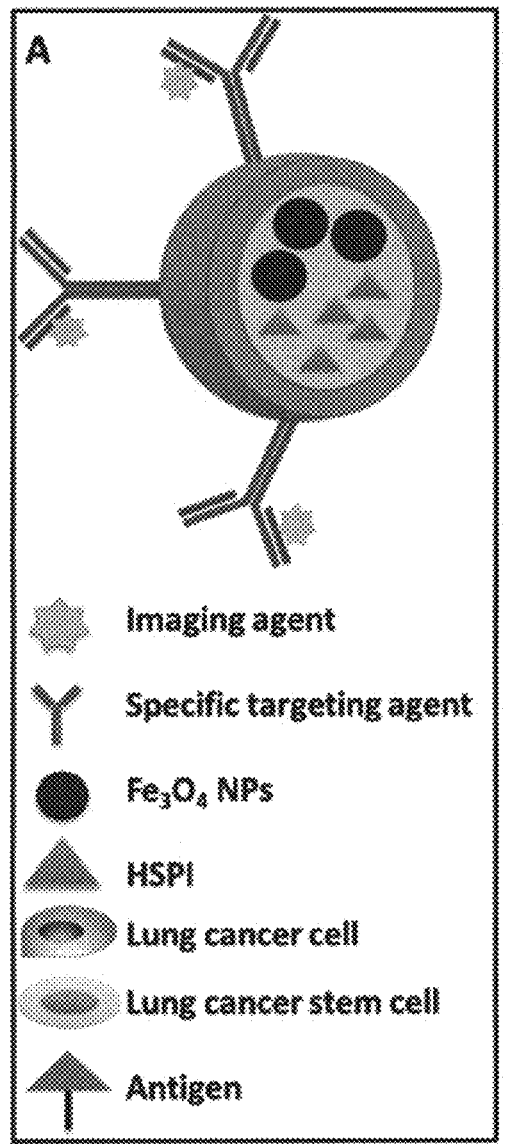
FIG. 1A is a schematic illustration of an embodiment of a nanoparticle composition according to the present invention.
Figure 1B:
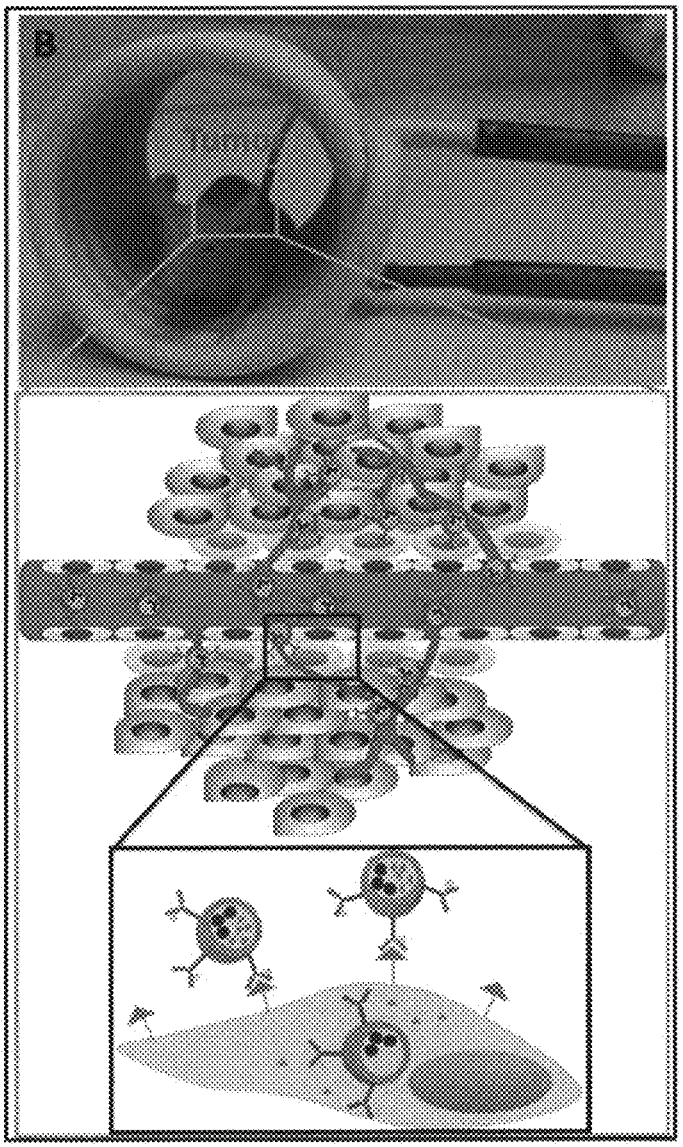
FIG. 1B is a schematic illustration of an embodiment of a treatment method of the present invention by targeting lung cancer stem cells (LCSCs) by way of simultaneous thermotherapy and chemotherapy by applying an alternating magnetic field (AMF)

Drug release studies were performed in a glass apparatus at 37° C. in AMF. The drug referred to is the nanoparticle composition described above. Please see FIG. 1A illustrating structure of the nanoparticle composition. The composition can be considered as an antibody modified thermal sensitive drug-loaded magnetic core-shell nanoparticle.

Firstly, HSPI-loaded Fe$_3$O$_4$@SiNPs was dispersed in 1 mL of medium and placed in a dialysis bag with a molecular weight cut-off of 10 kDa. The dialysis bag was then immersed in 9 mL PBS and kept in a horizontal laboratory shaker maintaining a constant temperature in AMF and stirring. Samples (300 mL) were periodically collected and the same volume of fresh medium was added. The amount of released HSPI was analyzed via UV-Visible spectrophotometry (PerkinElmer, PE Lamda 750, USA) and the concentration-absorbance standard equation. The drug release studies were performed in triplicate for each of the samples.

Multifunctional Nanoparticles Uptake by LCSCs

LCSCs ($3^{rd}$ generation) were seeded on coverslip in 24-well plate at a density of 1×10$^4$ cells/well and incubated at 37° C. for 24 h, then incubated with PE-CD20 labeled Fe$_3$O$_4$@SiNPs (CD20-Fe$_3$O$_4$@SiNPs) and Fe$_3$O$_4$@SiNPs at a final concentration of 100 µg/mL for 1 h and 24 h at 37° C. After nuclear staining with DAPI (1 mg/mL) for 5 min, the cells were washed, fixed and mounted in fluorescent mounting medium. Images were captured with a confocal microscope (SPE, Leica, Germany).

In Vitro Targeted Internalization

LCSCs ($3^{rd}$ generation) were seeded in the 24-well plate at a density of $1 \times 10^4$ cells/well. After 24 h incubation, cells were treated with 100 mg/mL CD20-$Fe_3O_4$@SiNPs and $Fe_3O_4$@SiNPs for 1 h. Following two washes with PBS, cells were collected and fixed with cold 2% glutaraldehyde in 0.1 M sodium cacodylate buffer at 4° C. for at least 2 h. The cells were post-fixed in 1% osmium tetroxide in 0.2 M sodium cacodylate buffer for 1 h and then stained with 2% aqueous uranyl acelate for 30 min at room temperature, followed by dehydration in a graded series of ethanol. Ultrathin sections of the samples were stained with uranyl acetate and lead citrate and then observed under transmission electron microscope (TEM) (FEI/Philips Tecnai 12 BioTWIN).

In Vitro Thermotherapy and Chemotherapy Under an Alternating Magnetic Field (AMF)

The AMF was generated by a 5 cm diameter 8-turn induction coil powered by a 3 kW alternating magnetic field generator. LCSCs were seeded in the 6-well plate at a density of $5 \times 10^4$ cells/mL. After 24 h incubation, cells were separately treated with 100 mg/mL CD20-$Fe_3O_4$@SiNPs, CD20-HSPI&$Fe_3O_4$@SiNPs, $Fe_3O_4$@SiNPs, HSPI&$Fe_3O_4$@SiNPs, SiNPs, and HSPI for 1 h. Cells without treatment were used as control. Following two washes with PBS, cells were placed inside the coil and heated to a defined temperature (between 37 and 50° C.) for 30 min. While frequency was kept constant at 350 kHz and temperature was monitored by using a thermometer immersed in a test tube containing 2 mL of solution. The traditional heating method (water bath heater) was used to compare with AMF heating. Cell survival was assessed by MTT assay.

Flow Cytometry Analysis

To detect the apoptosis and necrosis of LCSCs following the AMF hyperthermia and water bath heating, LCSCs were treated with CD20-HSPI&$Fe_3O_4$@SiNPs then washed with PBS and tested by Apoptosis Detection Kits (YO-PRO-1/7-AAD, Invitrogen) according to the manufacturer's protocol. Briefly, treated cells were stained with YO-PRO-1 and 7-AAD solution in the dark for 30 min, and then analyzed by flow cytometry (BD FACSCanto II system, BD Biosciences).

Building Human Lung Cancer Xenograft

BALB/c nude mice (5-6 weeks old and weighted 15-20 g) were provided from Queen Elizabeth Hospital (Hong Kong, China) and all animals received care in compliance with the guidelines outlined in the Guide for the Care and Use of Laboratory Animals. To setup the tumor model, LCSCs ($3 \times 10^4$ cells/200 µL) were injected into the subcutaneous space of back region of the mouse. Tumor growth in each mouse was closely observed every 4 days. The tumor volume can be calculated from the formula: length×width×depth×π/6.

Hemolysis Assay

Red blood cells (RBCs) were harvested from whole blood by centrifuging at 3000 rpm for 5 min, and then washed three times with saline. The obtained RBC (100 µL) were diluted with PBS to 1 mL. To evaluate the hemolytic effect, 500 µL of diluted RBC suspension was incubated with 50 µL CD20-HSPI&$Fe_3O_4$@SiNPs (final concentration 1 mg/mL) at 37° C. with gentle shaking. The final volume of the hemolysis assay in all experiments was 1.0 mL. 500 µL of diluted RBC suspension incubated with 500 µL PBS was used as the negative control. The same amount of RBCs incubated with 1 mL water was used as the positive control. After 1 h, the samples were centrifuged at 3000 rpm for 5 min. The absorbance of the supernatant was measured by microplate reader at 540 nm. The absorbance value of positive should be 0.8±0.3, while negative one should be less than 0.03. The percentage of hemolysis was calculated as the following equation: Hemolytic rate (%)=[($OD_{sample}$−$OD_{negative}$)/($OD_{positive}$−$OD_{negative}$)]×100%.

Immune Cell Analysis

To further investigate the side effects of nanoparticles on immune system of mice, the whole blood was collected into anticoagulant from NPs treated mice on day 1, 2, 3, 4, 5, 6, 7, and 40 post-injection. White blood cell populations were gated into lymphocytes, monocytes and macrophages, and neutrophils using forward and side scatter analysis in a flow cytometry. Number of B-Cell from lymphocytes was then analyzed with antibodies against typical B-cell antigens (CD20). Mice without NPs injection were used as control.

In Vivo Uptake of NPs in Bone Marrow-Derived Mesenchymal Stem Cells (MSCs)

For in vivo uptake of NPs in MSCs, the MSCs were isolated from NPs treated mice on day 40 post-injection according to previous work. The purified MSCs were analyzed using a FACSCalibur flow cytometry system. Mice without NPs injection were used as control.

Distribution of Multifunctional Nanoparticles in Nude Mouse Body

The lung cancer bearing mice were injected with CD20-HSPI&$Fe_3O_4$@SiNPs or HSPI&$Fe_3O_4$@SiNPs via the retro-orbital sinus. Images were taken at 0.5, 1, 2, and 24 h after injection using the in vivo imaging system (Xenogen IVIS® Spectrum). The nude mice were sacrificed at 24 h, and the ex vivo image of the organs including heat, liver, spleen, lung, kidney, and tumor were analyzed by the in vivo imaging system.

Efficacy of Combination Thermotherapy and Chemotherapy in Animal Models

When the tumor volume reached about 100 mm³, at about 10 days, the mice were randomly divided into five groups (n=10): CD20-$Fe_3O_4$@SiNPs, CD20-HSPI&$Fe_3O_4$@SiNPs, HSPI&$Fe_3O_4$@SiNPs, CD20-HSPI@SiNPs, and PBS. The samples (50 mg/kg) were injected to nude mice via the retro-orbital sinus once a week. One day after injection, the mice were then exposed to AMF (10 cm diameter 12-turn induction coil powered by a 3 kW alternating magnetic field generator) for 30 minutes (3 times each week). All mice body weight and tumor volume were measured every 4 days.

Staining of Tumor Xenograft and Organ Tissues

To further investigate the therapeutic effects of multifunctional NPs on tumor-bearing mice treated by retro-orbital sinus injection, the tumors were excised for immunohistochemical analysis on day 40 post-injection. Meanwhile, organs were collected for studying the side effects of multifunctional NPs on mice by immunohistochemical analysis. The tissue was fixed with 10% neutral buffered formalin, embedded in paraffin, sectioned at 5 µm thickness, and stained with hem atoxylin and eosin (H&E). The sections were then observed by a Digital Imaging System (Axioplan2, Zeiss).

Fluorescence staining of tumor xenograft sections was performed to confirm the significant therapeutic efficacy of multifunctional NPs to LCSCs. After blocking in serum, tissue sections were incubated with PE-conjugated CD20 antibody at 37° C. for 1 h. The stained tissues were examined under a confocal laser scanning microscope.

Statistical Analysis

All data were presented as mean±standard deviation (SD). Significant differences were determined using the Student's t-test where differences were considered significant ($p<0.05$).

Results

Characterization of Multifunctional Nanoparticles

Figure 1H:
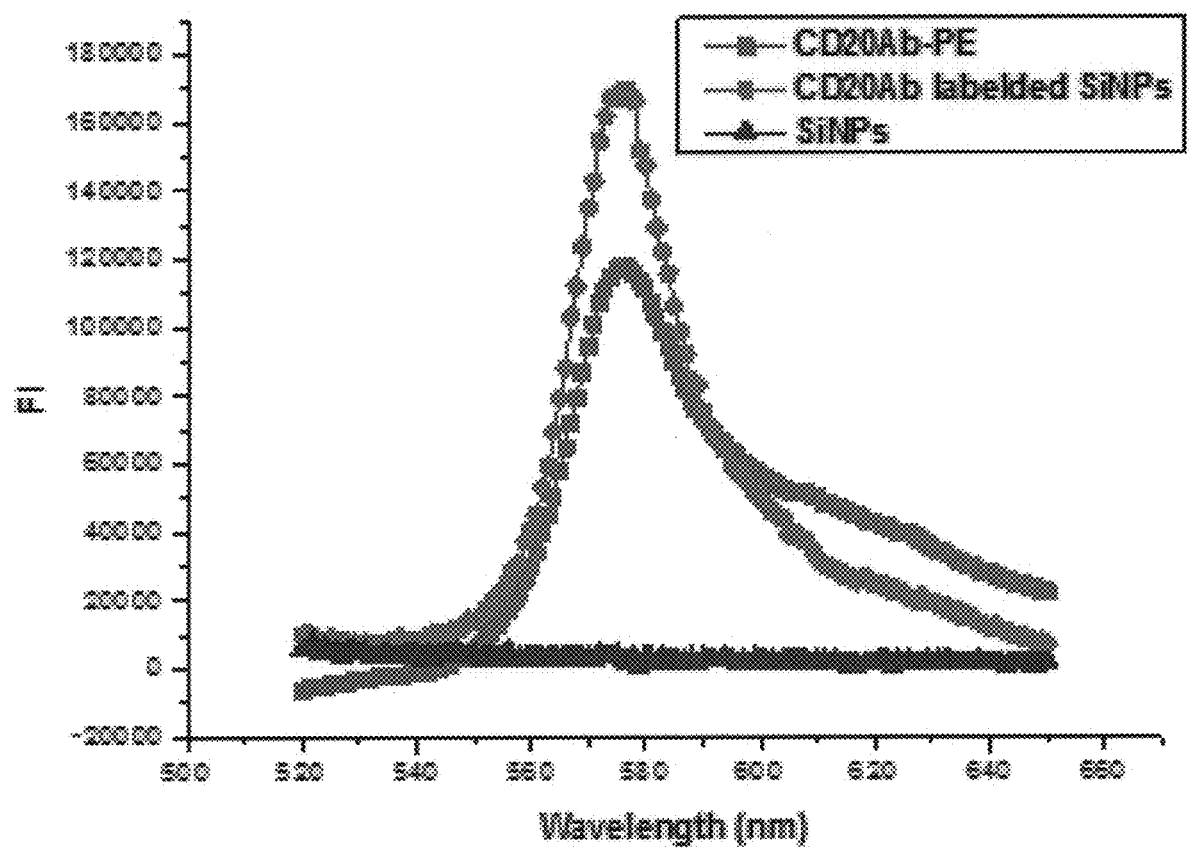
FIG. 1H is a graph showing fluorescence spectra of the Phycoerythrin (PE)-labeled CD20-$Fe_3O_4$@SiNPs.

TEM images showed that $Fe_3O_4$@SiNPs and CD20-$Fe_3O_4$@SiNPs were mono-dispersed in PBS buffer for few weeks without aggregation. Particle sizes were mostly between 35 nm to 40 nm and were narrowly distributed (FIGS. 1C and 1F). Conjugation with the PE-CD20 antibody slightly changed the particle sizes (FIG. 1D). As shown in FIG. 1E, the silica thickness was fine controlled from 15 nm to 20 nm and the diameter of $Fe_3O_4$ NPs core (dark color) was around 30 nm. The zeta potential results (FIG. 1G) showed that surface charge of the $Fe_3O_4$@SiNPs and CD20-$Fe_3O_4$@SiNPs was −42.86 and −22.04 mV, respectively. Furthermore, the conjugation of PE-CD20 antibody on surface of $Fe_3O_4$@SiNP was confirmed by fluorescent spectra using spectro-fluoro-meters (FluoroMax-4). As shown in FIG. 1H, the fluorescence signal of the PE-CD20 labeled NPs was located the same maximum emission wavelength at 580 nm as in a solution of free PE-CD20 antibody, indicating the successful conjugation of PE-CD20 antibody on the surface of HSPI&$Fe_3O_4$@SiNPs.

Magnetic Hyperthermia Property Study

Figure 2A:
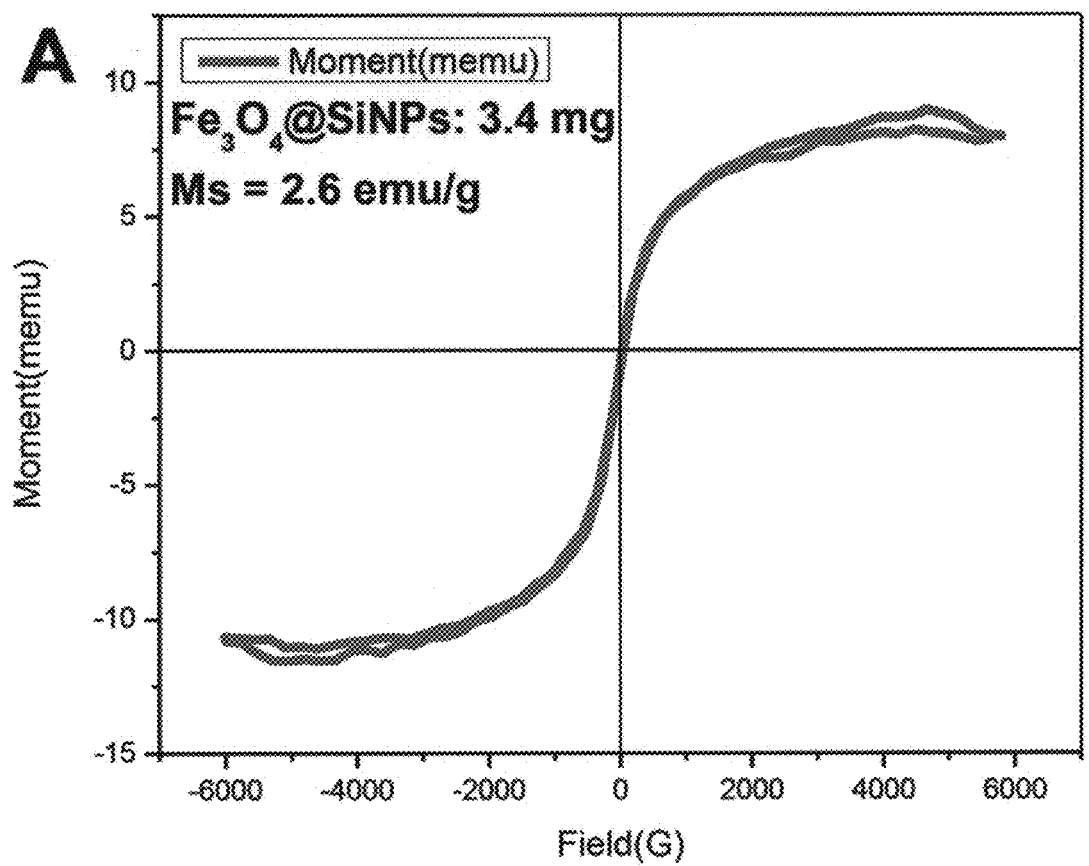
FIGS. 2A, 2B, 2C and 2D, are graphs showing magnetic hysteresis loops of i) $Fe_3O_4$@SiNPs, ii) $Fe_3O_4$ NPs, time course of the raised temperature of PBS, iii) SiNPs, and $Fe_3O_4$@SiNPs, and iv) in vitro release curve of HSPI-loaded $Fe_3O_4$@SiNPs, respectively.
Figure 2B:
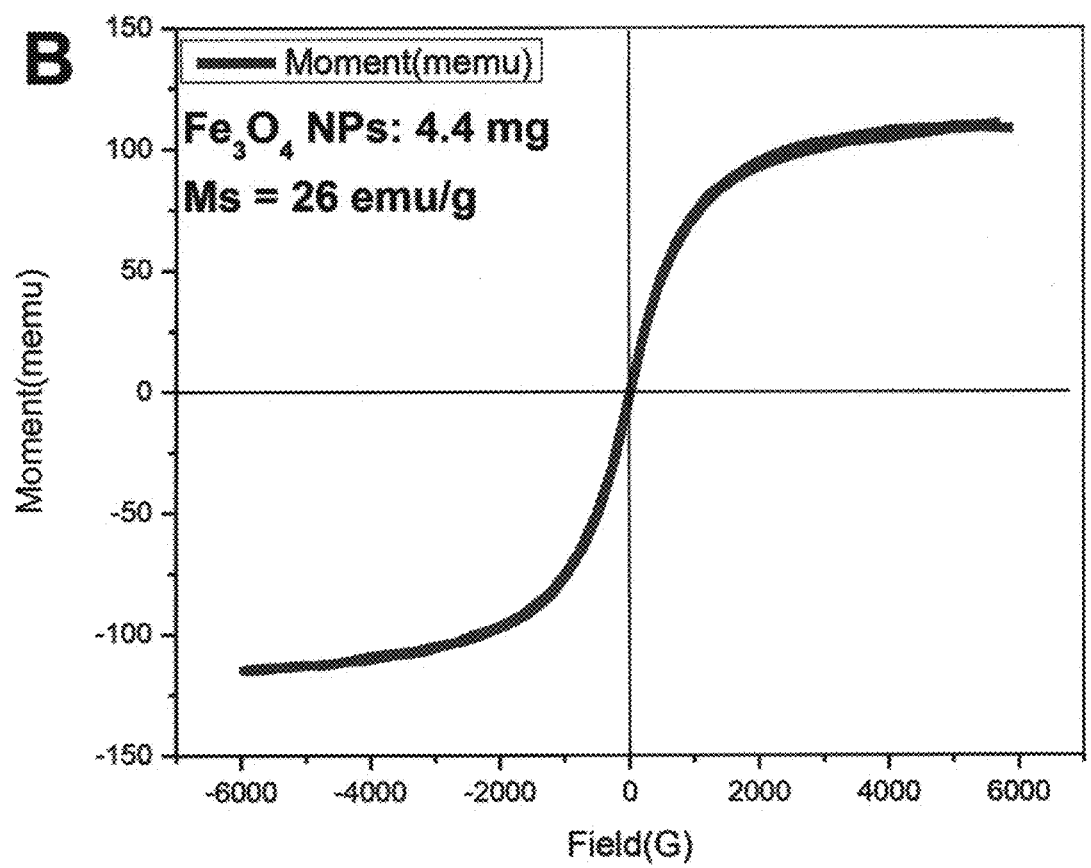

Hysteresis curves obtained from the vibrating sample magnetometer (VSM) showed that the saturation value of magnetization (Ms) of $Fe_3O_4$ NPs and CD20-$Fe_3O_4$@SiNPs. The curve passed through the origin indicated that both $Fe_3O_4$ NPs and $Fe_3O_4$@SiNPs were superparamagnetic. As shown in FIGS. 2A and 2B, the Ms of $Fe_3O_4$ NPs and CD20-$Fe_3O_4$@SiNPs were 26 emu/g and 2.6 emu/g, respectively. $Fe_3O_4$@SiNP has a weaker magnetization than the naked $Fe_3O_4$ NPs under the same strength of applied magnetic field because the strength of magnetization is related to the amount of magnetic material in the sample.

Figure 2C:
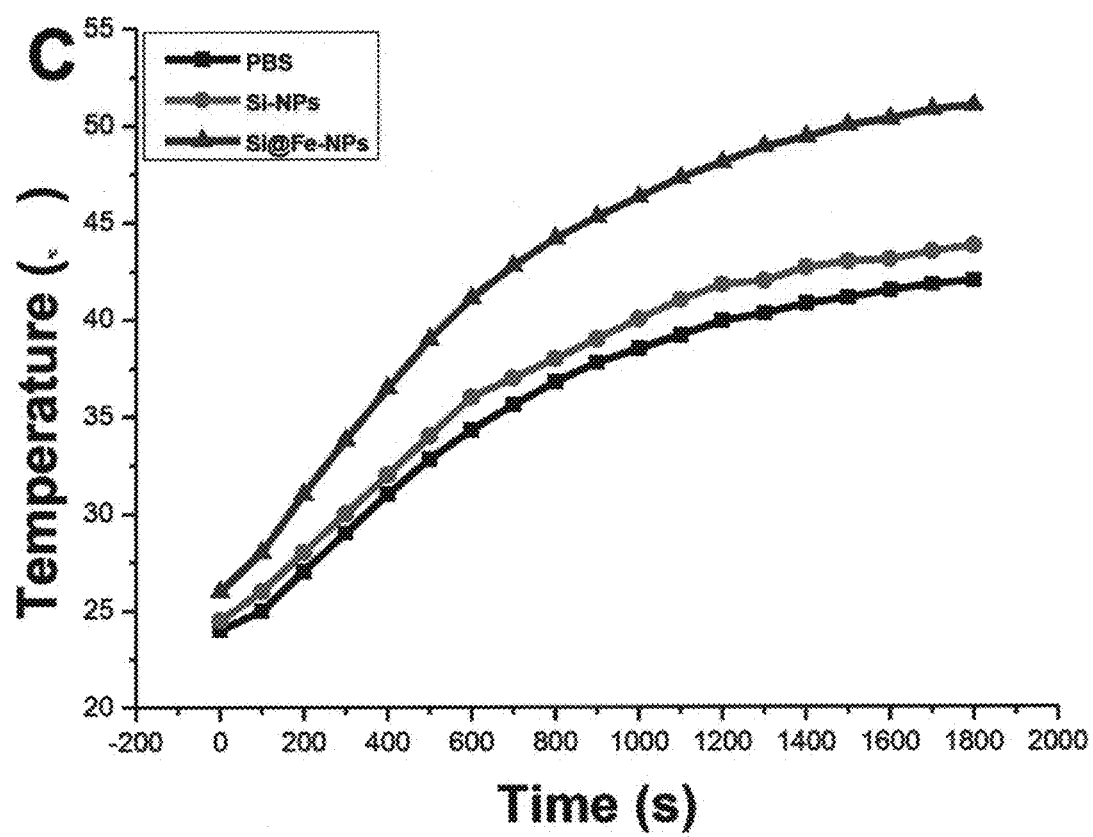

A high Ms value is desirable to enhance the heating rate of the NPs under an AMF. The comparative temperature rise of the NPs suspensions against the exposure time is shown in FIG. 2C. The highest temperatures achieved by $Fe_3O_4$@SiNPs suspension was 50.5° C., when compared the SiNPs suspension and PBS solution. Thus, with even dispersion of the NPs in a neutral medium and effective heating, $Fe_3O_4$@SiNPs are a strong candidate for magnetic hyperthermia as well as other biomedical applications such as heat-triggered drug delivery systems.

The data in FIGS. 2A to 2D are expressed as mean±SD for n=3.

In Vitro Drug Release Study

Figure 2D:
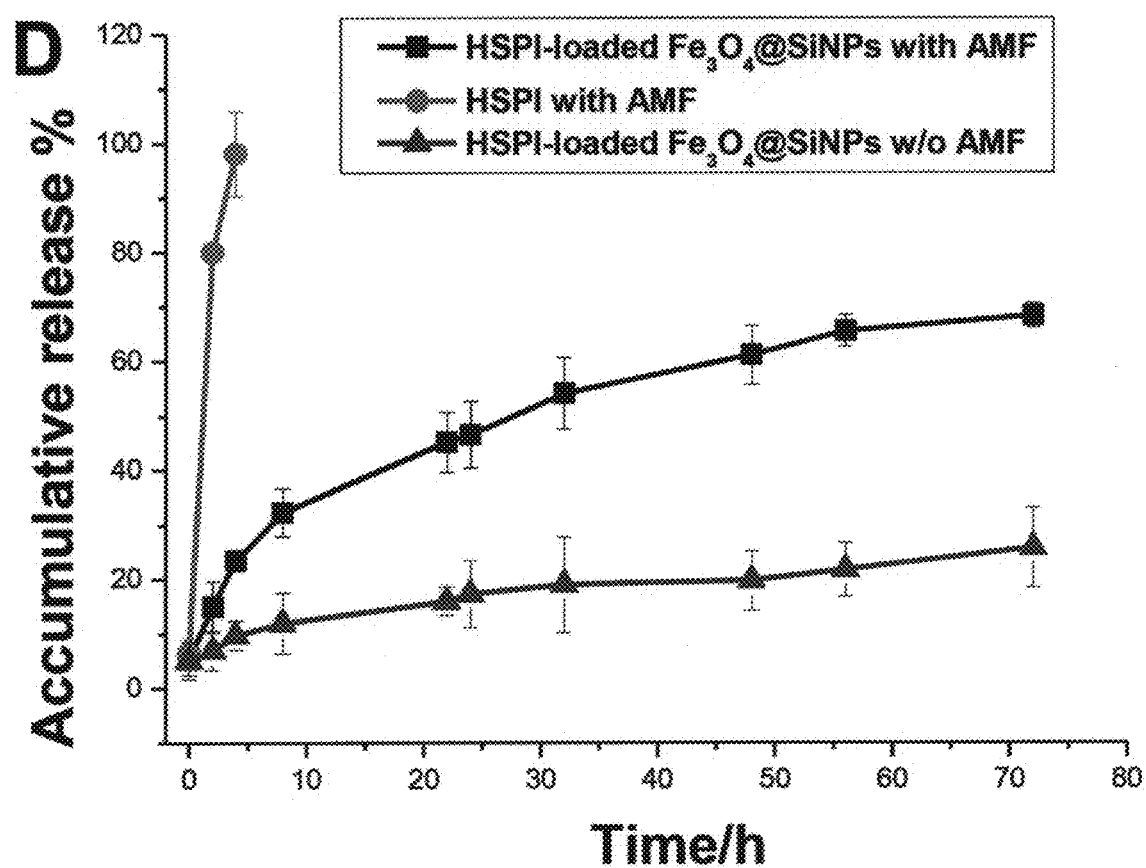

Controlled and sustained drug release is very important for drug delivery systems. FIG. 2D depicts the accumulative release profile of HSPI from the $Fe_3O_4$@SiNPs with the concentration of 1 mg/mL. An in vitro release study showed that the $Fe_3O_4$@SiNPs exhibited sustained release of the HSPI for up to 72 h (70% release) under AMF, which can achieve the controlled release in animal body. However, only 21.5% drug release rate was observed for up to 72 h without AMF trigger.

In Vitro Cellular Uptake and Internalization

Figure 3:
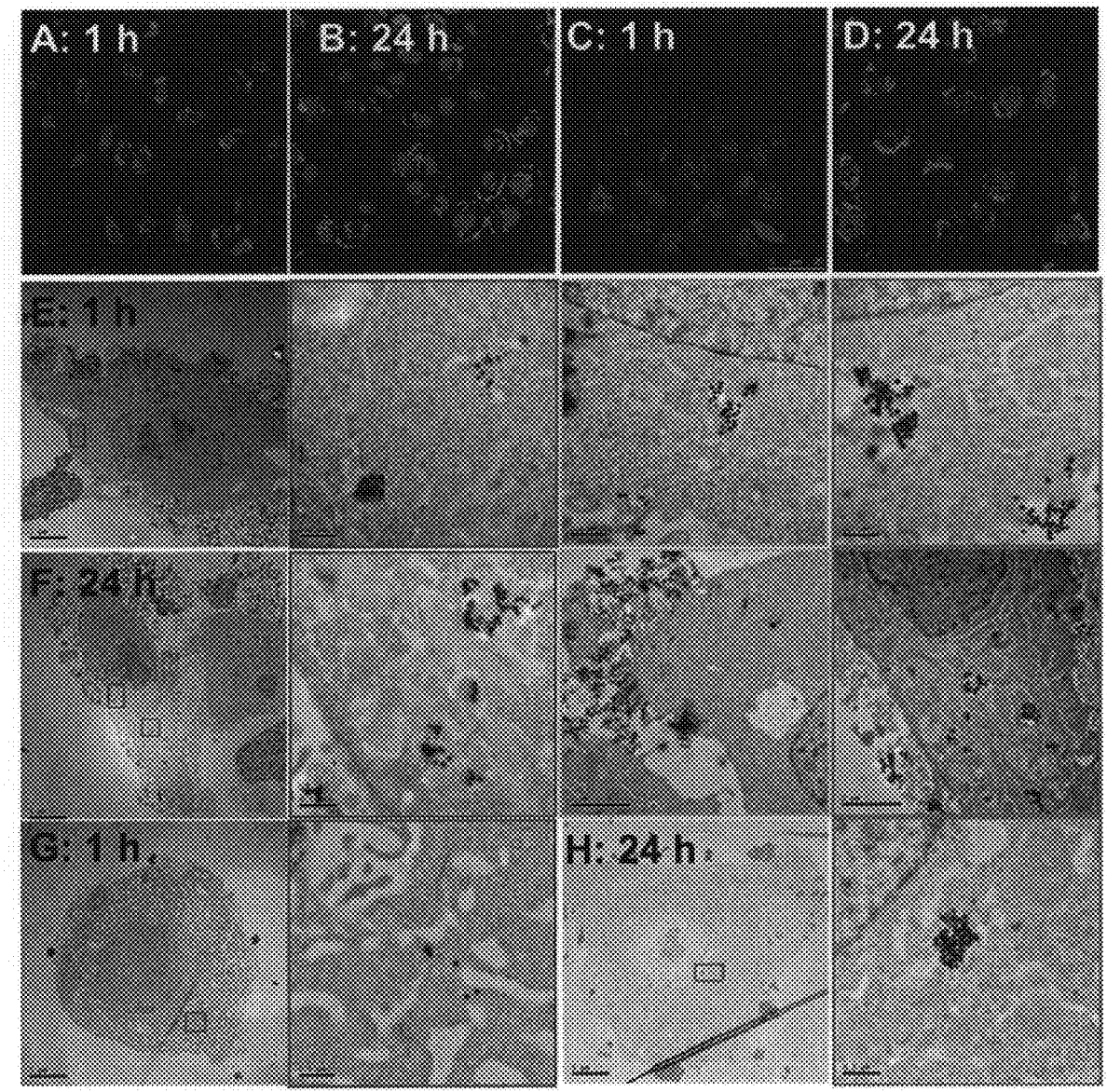
FIG. 3 are confocal fluorescence and transmission electron microscopic (TEM) images showing in vitro cellular uptake and internalization of CD20-$Fe_3O_4$@SiNPs and $Fe_3O_4$@SiNPs by a type of lung cancer stem cells (LCSCs)

The cellular uptake of $Fe_3O_4$@SiNPs and CD20-$Fe_3O_4$@SiNPs was investigated by LCSCs (high expressing CD20) using laser confocal scanning microscopy. The LCSCs ($3^{rd}$ generation) were incubated with $Fe_3O_4$@SiNPs and CD20-$Fe_3O_4$@SiNPs at 37° C. for 1 h and 24 h with the concentration at 100 μg/mL. FIG. 3, including A to H, demonstrated that the uptake of CD20-$Fe_3O_4$@SiNPs by LCSCs was higher than that of $Fe_3O_4$@SiNPs after 1 h incubation. This result also indicates that CD20-labeled $Fe_3O_4$@SiNPs entered cells more quickly than free $Fe_3O_4$@SiNPs, which might be due to the receptor-mediated endocytosis pathway. Besides that, cellular uptake increased as the incubation time increased from 1 h to 24 h. FIG. 3 shows confocal images of cells treated with CD20-$Fe_3O_4$@SiNPs (FIG. 3-A and FIG. 3-B) and $Fe_3O_4$@SiNPs (FIG. 3C and FIG. 3-D) for 1 h and 24 h. FIG. 3 also show TEM images showing internalization of CD20-$Fe_3O_4$@SiNPs (FIG. 3-E and FIG. 3-F) and $Fe_3O_4$@SiNPs (G and H) by LCSCs.)

Based on the results of the cellular uptake by LCSCs, the internalization of NPs was further studied through TEM. As shown in FIGS. 3E and 3F, the CD20-$Fe_3O_4$@SiNPs were observed aggregated and internalized near the cell membrane after 1 h incubation, and thereby deeply localized in lysosomes and in cytoplasm. However, less $Fe_3O_4$@SiNPs (FIGS. 3-G and 3-H) was localized in lysosomes or in cytoplasm even after 24 h incubation, indicating that CD20 facilitated the targeted receptor internalization efficacy.

Figure 4A:
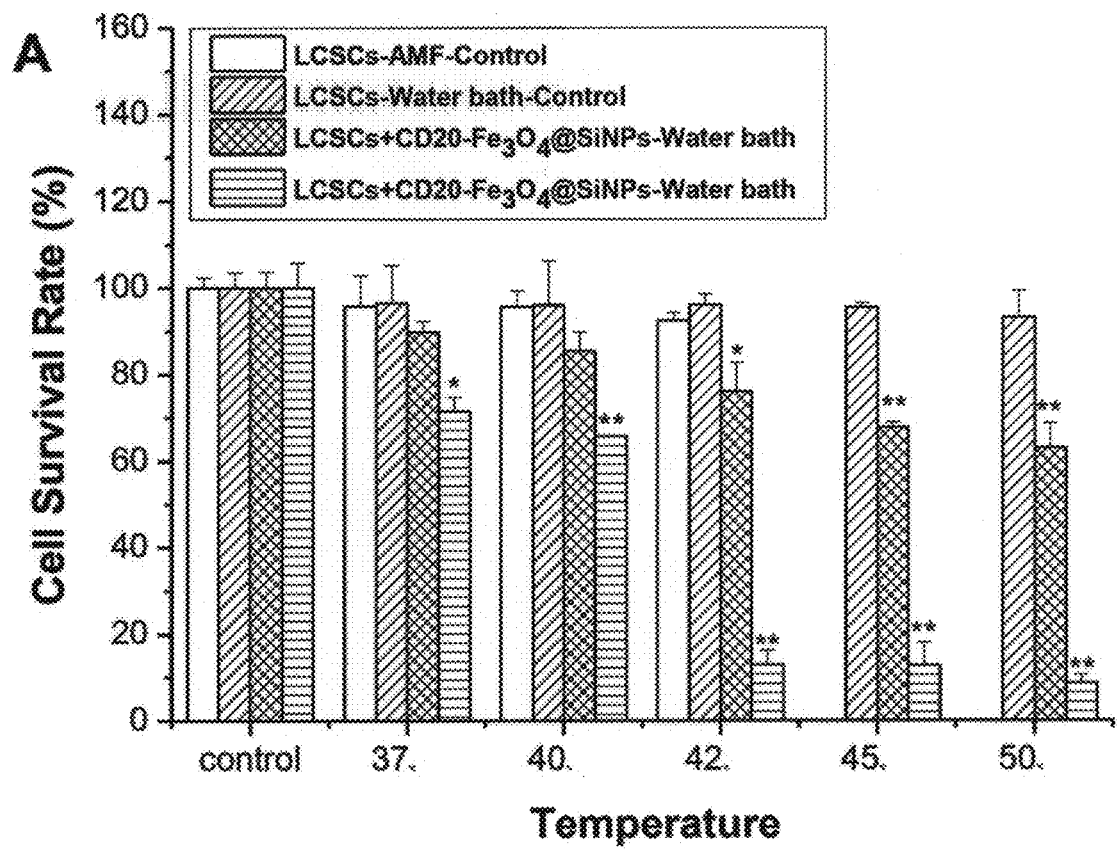
FIG. 4A is a graph showing relative survival rate of LCSC after heat treatment.

In Vitro Thermotherapeutic and Chemotherapeutic Effects of Multifunctional NPs on LCSCs To evaluate the thermotherapeutic effects of CD20-$Fe_3O_4$@SiNPs, the survival of LCSCs was tested by MTT assay after 30 min treatment under AMF or in water bath at defined temperature. As shown in FIG. 4A, cells survival rates of 76%, 68%, and 63% can be observed when they were treated with CD20-$Fe_3O_4$@SiNPs and heated at 42, 45, and 50° C. in water bath. (The temperature was controlled by water bath or AMF at 37° C., 40° C., 42° C., 45° C., and 50° C. for 30 min, respectively.) This result shows that LCSC had the property of thermos-resistance due to the high expression of members of heat shock protein (HSP) family. On the contrary, only about 12% of LCSCs can survive at 42° C. after the AMF heating process. Furthermore, only about 8% of LCSCs can survive while temperature was kept at 50° C. under AMF treatment. This result illustrated that LCSCs were sensitive to AMF controlling CD20-$Fe_3O_4$@SiNPs-mediated thermotherapy. However, the high temperatures not only can kill cancer cells, but they also can injure or kill normal cells and tissues. To achieve the aim of selectively eliminating LCSCs at lower temperature, HSP90 inhibitor 17-(Dimethylaminoethylamino)-17-demethoxygeldanamycin (17-DMAG) was encapsulated in CD20-$Fe_3O_4$@SiNPs to inhibit the expression of HSP90 and overcome the thermoresistance of LCSCs.

Figure 4B:
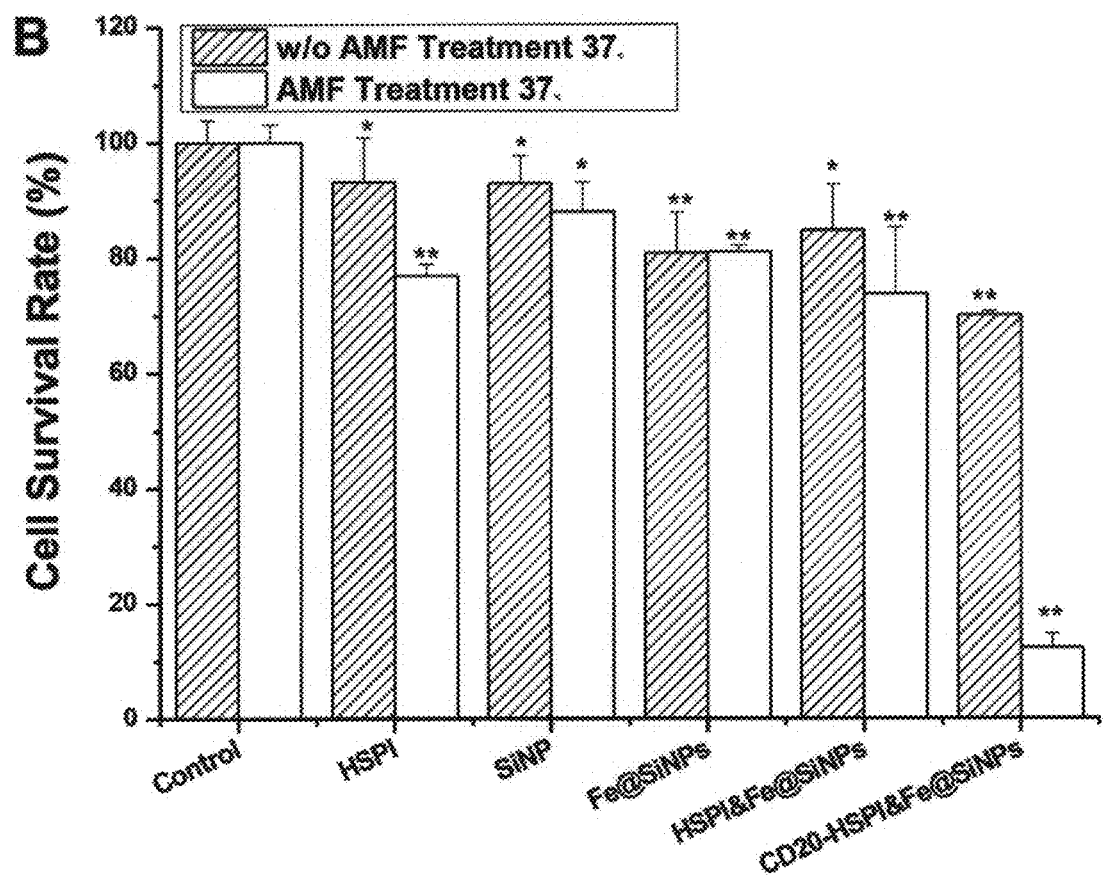
FIG. 4B is a graph showing relative survival rate of LCSC after nanoparticle-mediated thermotherapy and chemotherapy.

To test combinatorial thermotherapeutic and chemotherapeutic effects of CD20-HSPI&$Fe_3O_4$@SiNPs, LCSCs were incubated with NPs and heated at 37° C. under AMF for 30 min. It can be noted that, compared with the control (medium only), there was significant decrease in the survival rate (about 12%) of LCSCs in the presence of CD20-HSPI&$Fe_3O_4$@SiNPs. Please see FIG. 4B. (The temperature was controlled by water bath or AMF at 37° C. for 30 min. Data were present as mean±SD, *$p<0.05$ and **$p<0.01$ indicate significant difference, n=5). On the other hand, the cell survival rate decreased to 77%, 88%, 81%, and 73% (FIG. 4B) in the presence of HSPI, SiNPs, $Fe_3O_4$@SiNPs, and HSPI&$Fe_3O_4$@SiNPs by applying AMF, respectively. The results demonstrated the high selective anti-tumor efficacy of CD20-HSPI&$Fe_3O_4$@SiNPs combined thermotherapy and chemotherapy under AMF. From FIG. 4B, it is shown that when heat shock protein inhibitors, magnetic nanoparticles, and a combination of heat shock protein inhibitors and magnetic nanoparticles are separately used, the efficacy of the composition, while noticeable, does not differ by much. However, when a combination cancer stem cell antibodies, heat shock protein inhibitors and magnetic nanoparticles are simultaneously used, the survival rate of the cancer stem cells is reduced at least three times, suggesting the unexpected synergistic effect of the combination.

Necrosis Induced by Multifunctional NPs-Mediated Thermotherapy and Chemotherapy

Figure 4C:
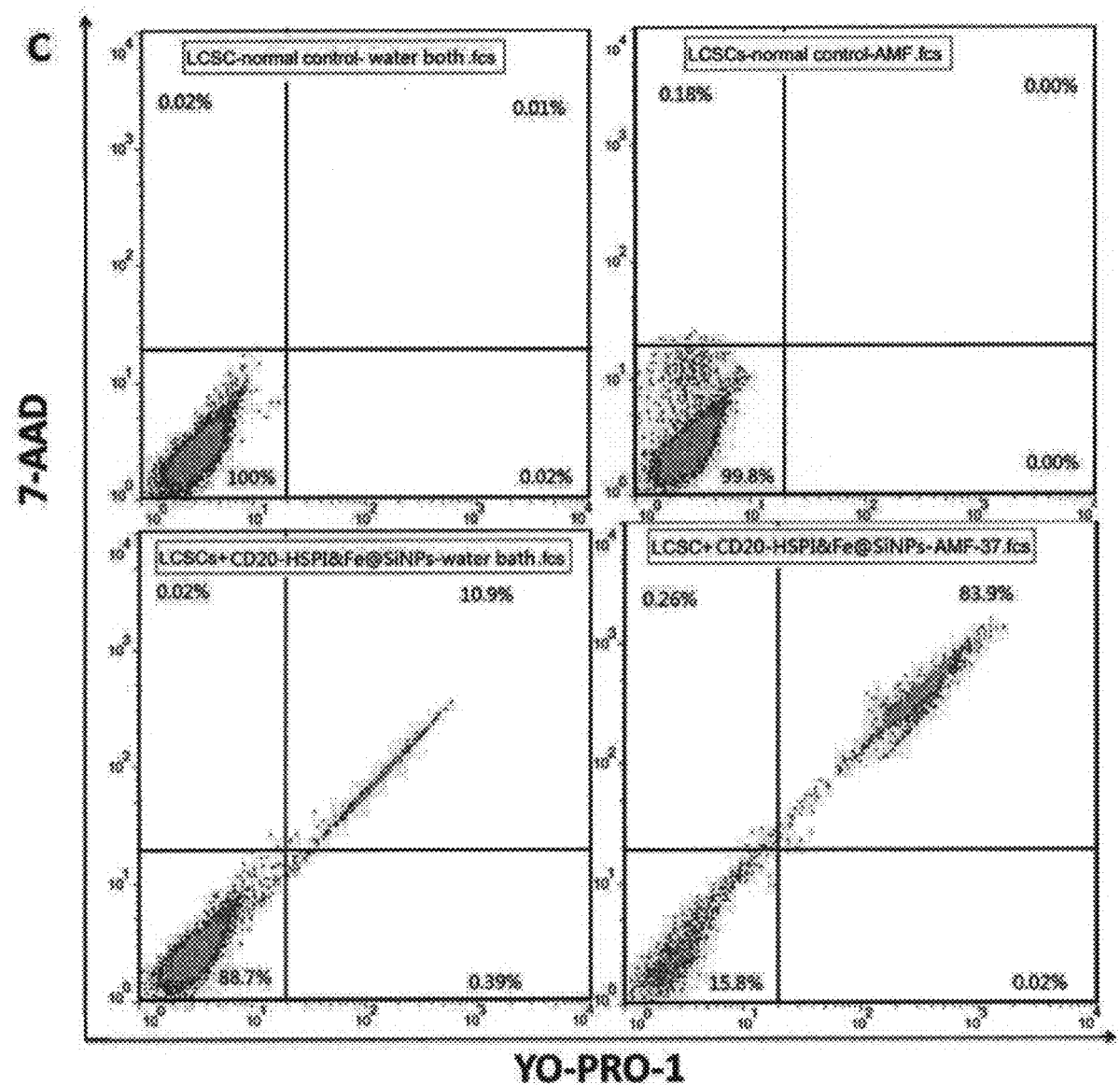
FIG. 4C is representative dot plots of LCSCs showing 7-AAD uptake and YO-PRO1 labeling as a function of time post heat treatment.

To understand the mechanism of cell death caused by multifunctional NPs-mediated thermotherapy and chemotherapy, LCSCs were treated by either water bath or AMF at 37° C. for 30 min and measured YO-PRO1 labeling (a marker of apoptosis) and 7-AAD permeability (an indicator of plasma membrane integrity). Consistent with above findings, water bath hyperthermia did not lead to robust cell death. The 7-AAD and YO-PRO1 positive cells were not observed after heating process in water bath (FIG. 4C). In contrast, both of 7-AAD and YO-PRO1 positivity in LCSCs treated with CD20-HSPI&$Fe_3O_4$@SiNPs reached to 83.9%. However, the apoptotic cells (YO-PRO1 positivity, 7-AAD negativity) were not observed after AMF treatment, indicating that necrosis was the predominant form of cell death observed in LCSCs. The nanoparticle-mediated combined thermotherapy and chemotherapy caused critical membrane damage to cells and consequent necrotic cell death.

In Vivo Tumor-Targeted Accumulation and Whole Body Distribution

Figure 10A:
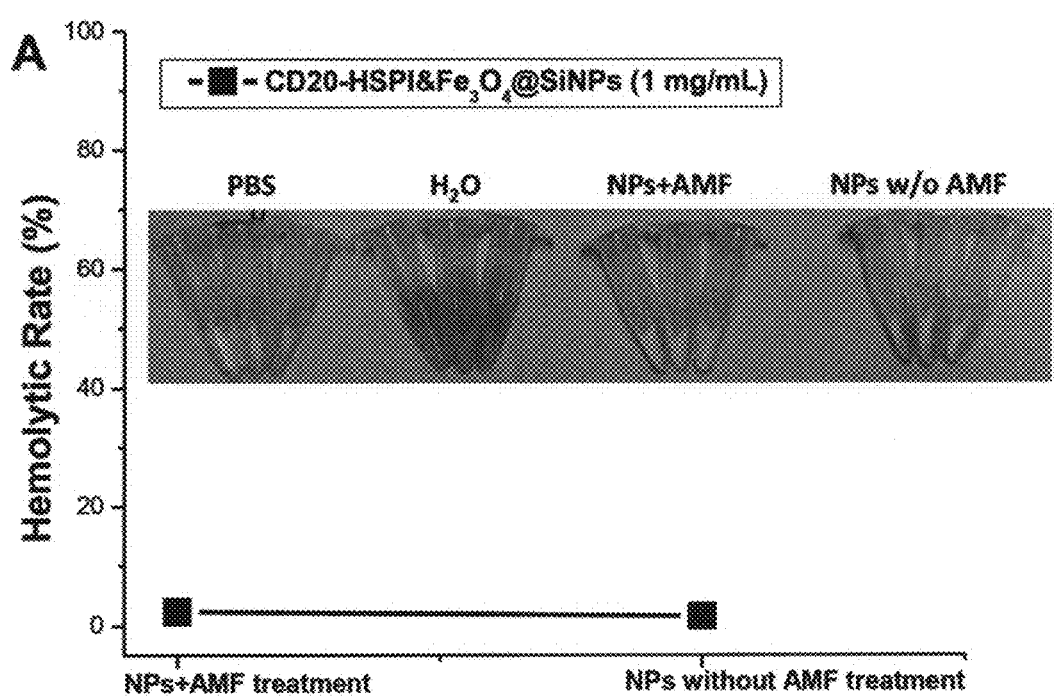
FIG. 10A and FIG. 10B are results of evaluation of hemolysis of CD20-HSPI&Fe$_3$O$_4$@SiNPs at concentrations of 1 mg/mL in PBS, using water as a positive control and PBS as a negative control; and flow cytometry analysis of lymphocytes, monocytes and macrophages, and neutrophils in white blood cell populations by forward and side scatter analysis, respectively.
Figure 10B:
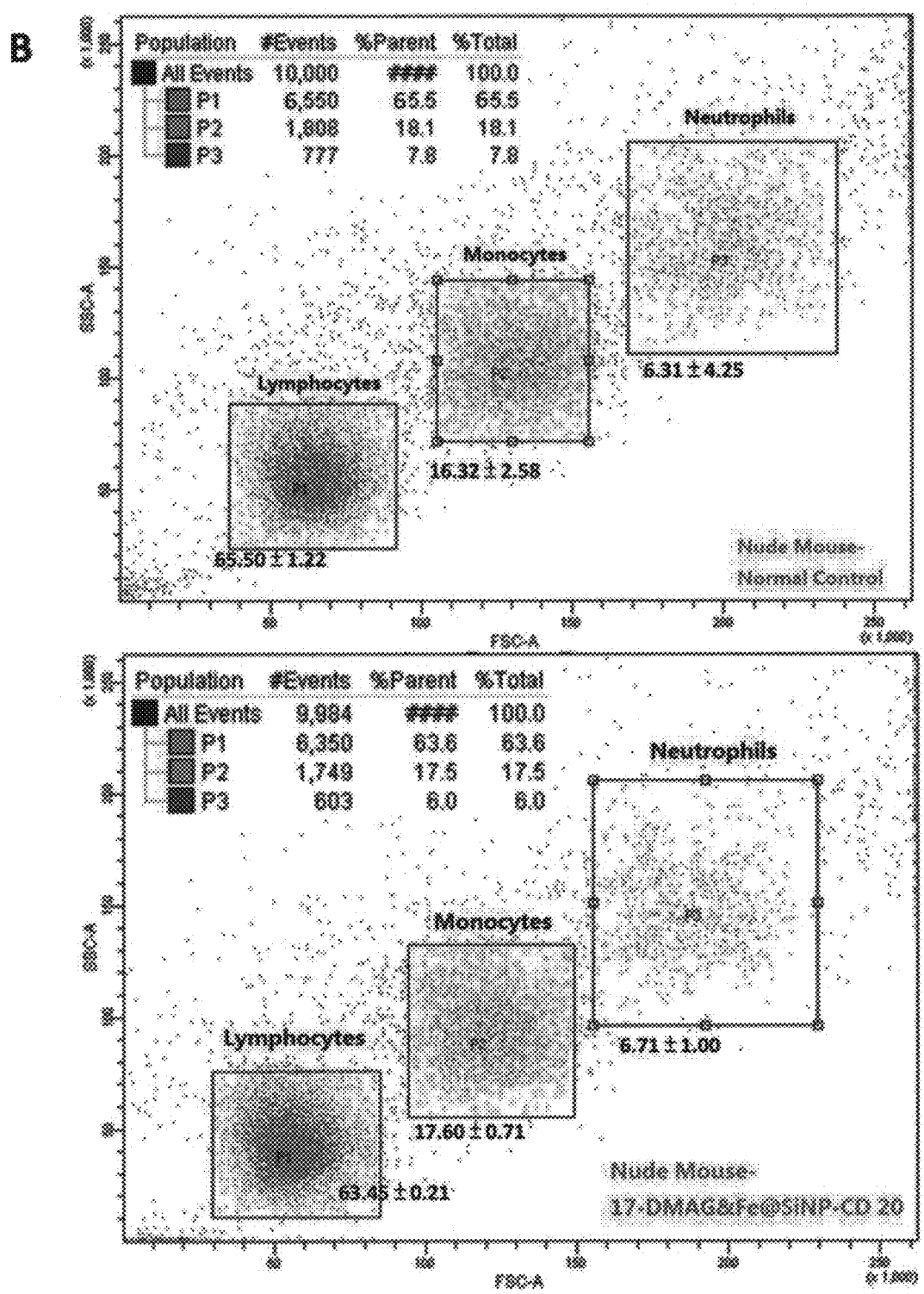

Before evaluating the tumor targeting and therapeutic efficacy in mice, the blood compatibility of CD20-HSPI&$Fe_3O_4$@SiNPs was evaluated by hemolysis assay and whole blood analysis. For hemolysis analysis, if erythrocytes are lysed, hemoglobin will be released and the supernatant will appear red that can be measured the absorbance at 540 nm. As shown in FIG. 10A, no visible hemoglobin was observed at the high concentration of 1 mg/mL, indicating that the multifunctional NPs had good hemocompatibility (<4% hemolysis). To evaluate the effects of multifunctional NPs on the white blood cells, mice were injected with NPs and treated under AMF for 30 min. White blood cell populations were gated into lymphocytes, monocytes, and neutrophils using forward and side scatter analysis in a flow cytometry. The results in FIG. 10B shows that there was no significant difference in immune cells number between control and NPs treated. These results demonstrated that the multifunctional NPs with good blood compatibility can be used for in vivo experiments.

The tumor-targeting efficacy and whole body distribution of CD20-HSPI&$Fe_3O_4$@SiNPs in tumor-bearing mice was then investigated by the in vivo imaging system.

Figure 5:
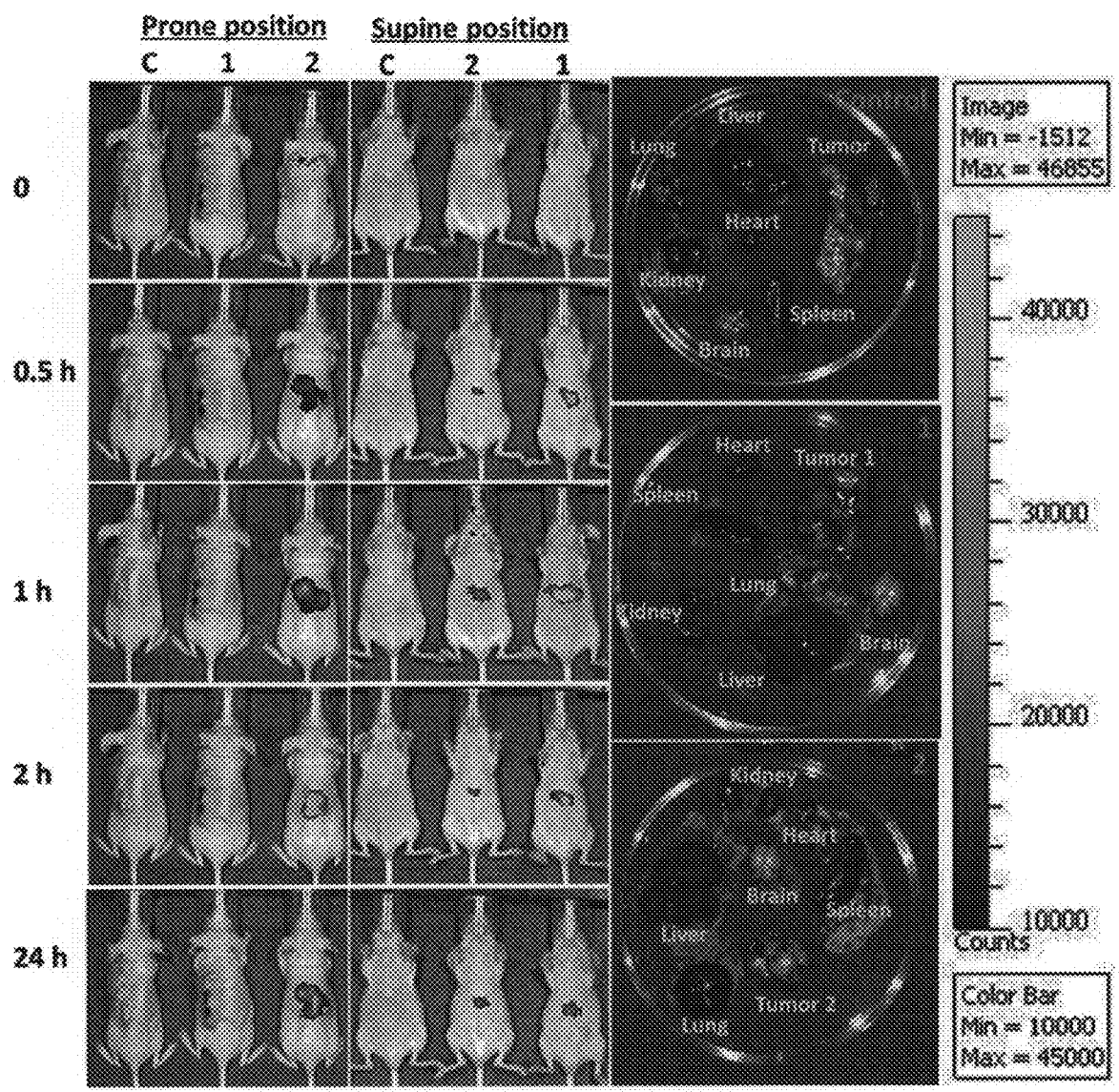
FIG. 5 are in vivo and ex vivo images of mice after intravenous injection of (PE)-labeled CD20-Fe$_3$O$_4$@SiNPs.

FIG. 5 shows that the fluorescence signals of CD20-$Fe_3O_4$@SiNPs and $Fe_3O_4$@SiNPs, both encapsulating a fluorescent dye Ru(bppy)$_3$, were all located in the liver at 30 min after injection. The results shows at 0.5, 1, 2, and 24 h treated with CD20-$Fe_3O_4$@SiNPs and $Fe_3O_4$@SiNPs (retro-orbital sinus injection). Most $Fe_3O_4$@SiNP gathered at the liver, while CD20-$Fe_3O_4$@SiNP was mainly concentrated in the tumor region. (C: control; 1: $Fe_3O_4$@SiNPs injection; 2: CD20-$Fe_3O_4$@SiNPs injection)

As time elapsed, the fluorescent signal in the CD20-$Fe_3O_4$@SiNPs treated mice was notably observed in tumor site. At 24 h time point post-injection, CD20-$Fe_3O_4$@SiNPs fluorescence signals were almost located around the tumor with a little amount of accumulation in liver. However, no detectable signal was recorded from the $Fe_3O_4$@SiNPs in tumor. CD20-$Fe_3O_4$@SiNPs were specifically targeted to tumor with greater efficiency than $Fe_3O_4$@SiNPs. The specific targeting efficiency and tumor-accumulation of CD20-$Fe_3O_4$@SiNPs was further confirmed by ex vivo imaging (FIG. 5) compared to $Fe_3O_4$@SiNPs. No obvious fluorescence signal was observed in the spleen, lung, heart, kidney, with a little amount of accumulation in liver, which was excreted in 24 h.

Figure 6A:
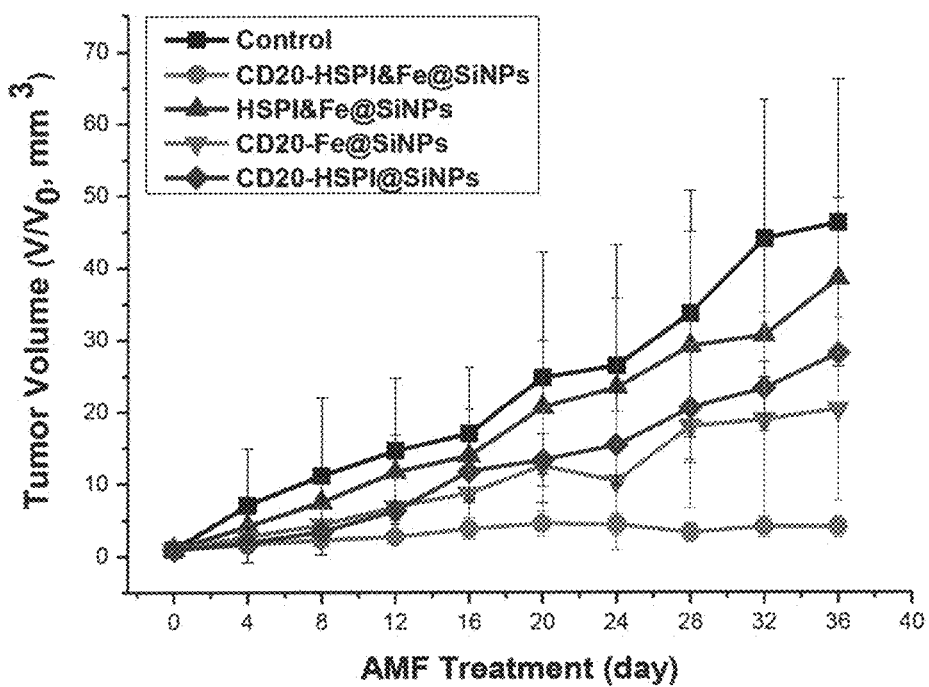
Figure 6B:
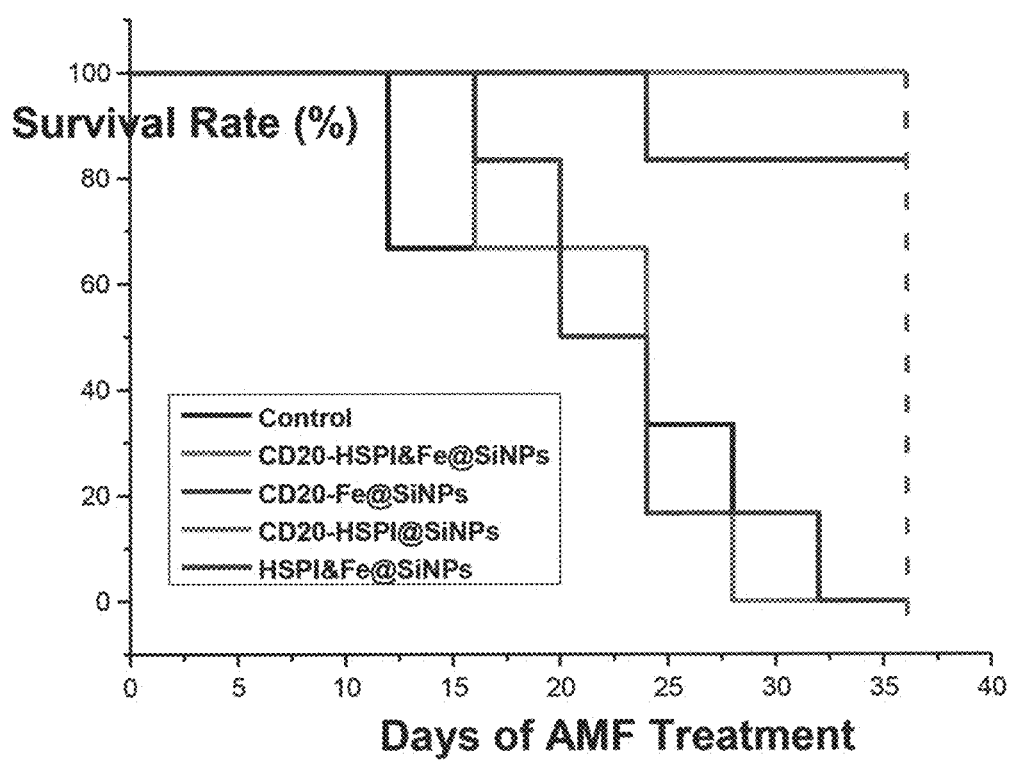
Figure 6C:
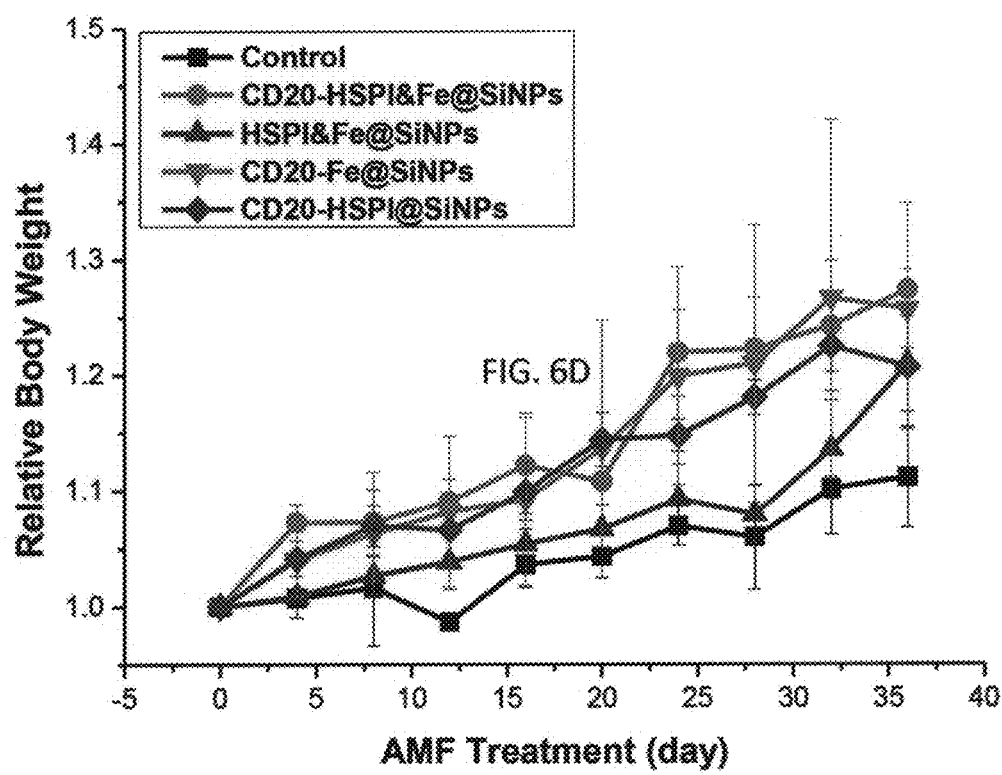
Figure 6D:
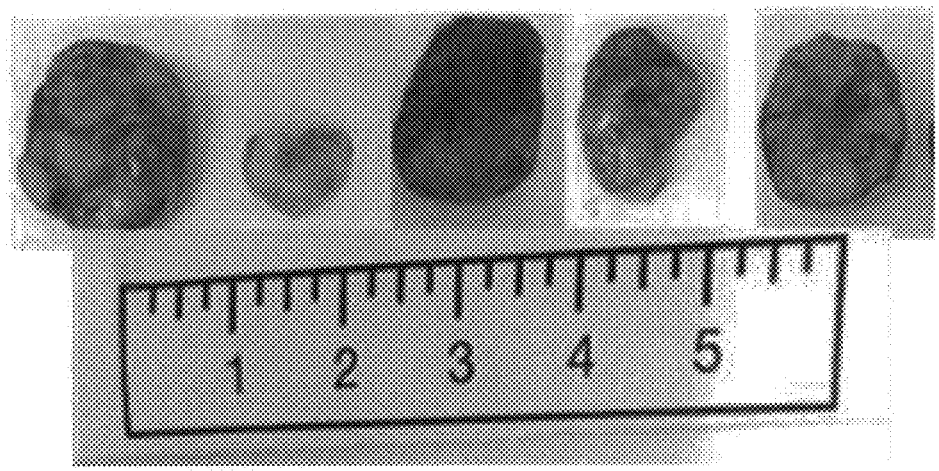

In Vivo Inhibition of Tumor Growth by Multifunctional NPs-Mediated Thermo- and Chemo-Therapy To determine the efficacy of CD20-HSPI&$Fe_3O_4$@SiNPs in antitumor combined thermotherapy and chemotherapy, LCSCs were xenografted to the back of nude mice in several experimental groups (n=10). The current model is a high degree malignancy tumor model, and the tumor volume increased to about 1500 mm$^3$ within 14 days. A total tumor volume more than 2000 mm$^3$ deemed moribund or death by veterinary consult. CD20-HSPI&$Fe_3O_4$@SiNPs dispersed in normal PBS were injected into the tumor-bearing mice by the retro-orbital sinus. The mouse was placed in a water-cooled magnetic induction coil with a diameter of 10 cm. Following treatment, the tumor volume was monitored for up to 36 days. As shown in FIGS. 6A and 6B, a fast tumor growth curve was obtained in the control group. (In FIG. 6A, there is shown nude mice xenografted with LCSCs before AMF treatment and 36 days after AMF treatment; FIG. 6B is a graph showing cumulative survival rate of nude mice injected with NPs; FIG. 6C is a graph showing relative body weight of the mice after treatment with various nanoparticles; FIG. 6D is a photograph image showing subcutaneous tumors after injection with NPs (2: CD20-HSPI&$Fe_3O_4$@SiNPs; 3: HSPI&$Fe_3O_4$@SiNPs; 4: CD20-$Fe_3O_4$@SiNPs; 5: CD20-HSPI@SiNPs). Data are presented as mean±SD, (n=10).)

Referring to FIG. 6A specifically, it is to be noted that even in the presence of antibodies configured to target cancer stem cells, the efficacy of the composition can vary widely. Referring to the green curve, when the composition further includes a heat shock protein inhibitor only, the tumor was able to grow from 0 mm$^3$ to about 30 mm$^3$. Referring to the purple curve, when the composition instead includes magnetic nanoparticles only, the tumor was still able to grow from 0 mm$^3$ to about 20 mm$^3$·th to about 30 mm$^3$. To the contrary, when the composition includes both the antibodies and the heat shock protein inhibitor (i.e. CD20-HSPI&$Fe_3O_4$@SiNPs), the tumor growth in the relevant group (please see red curve in FIG. 6A) was dramatically inhibited to no apparent growth. For comparison, treatment with unmodified HSPI&$Fe_3O_4$@SiNPs, CD20-$Fe_3O_4$@SiNPs or CD20-HSPI@SiNPs did not significantly affect tumor growth. The mean survival period of mice treated with CD20-HSPI&$Fe_3O_4$@SiNPs was extended to 36 days from 12 days for the control groups (FIG. 6B). The body weight of each group increased proportionately during the observation period (FIG. 6C). The mice treated with PBS had the lowest body weight in comparison with the mice in other groups. The synergistic effect of the composition of the antibodies and the heat shock protein inhibitor essentially provides a total suppression of tumor group. When comparing with disclosure from prior art, the extent of synergistic effects is not only significantly larger but unexpected. It is to be noted that the use of CD20 is particular preferred in that it can target the cancer stem cells effectively. While in the past there was no or little report showing the effective of targeting cancer stem cells by CD20. This significant in that cancer cells and cancer stem cells are pathologically rather different.

Figure 7A:
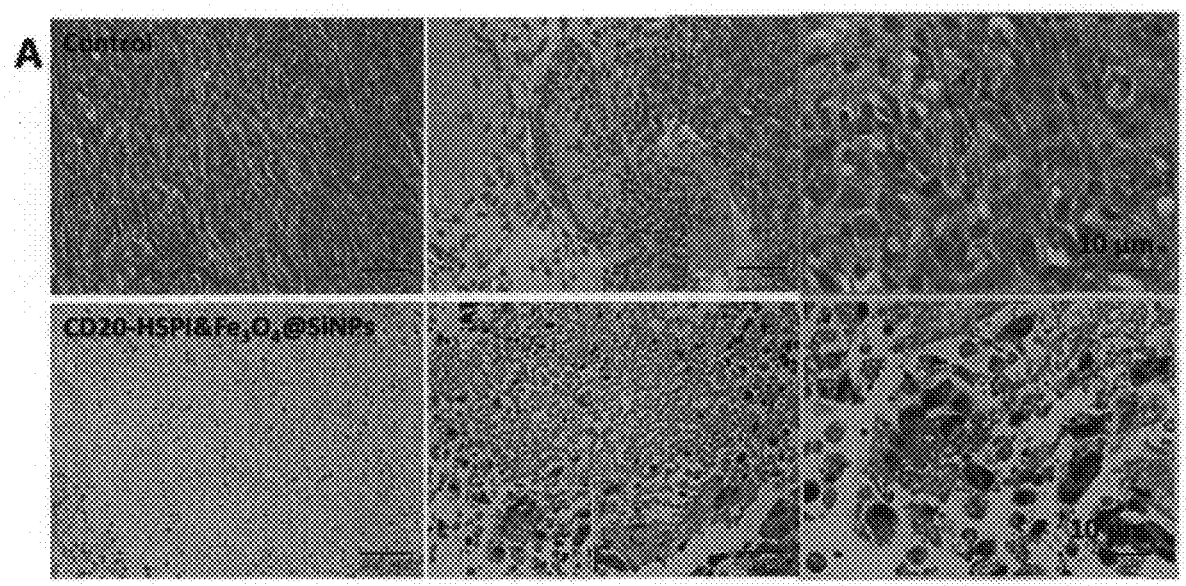
FIG. 7A are images showing H&E stained tumor tissue sections of control and CD20-HSPI&Fe$_3$O$_4$@SiNPs treated mice at 36 days after AMF treatment.
Figure 7B:
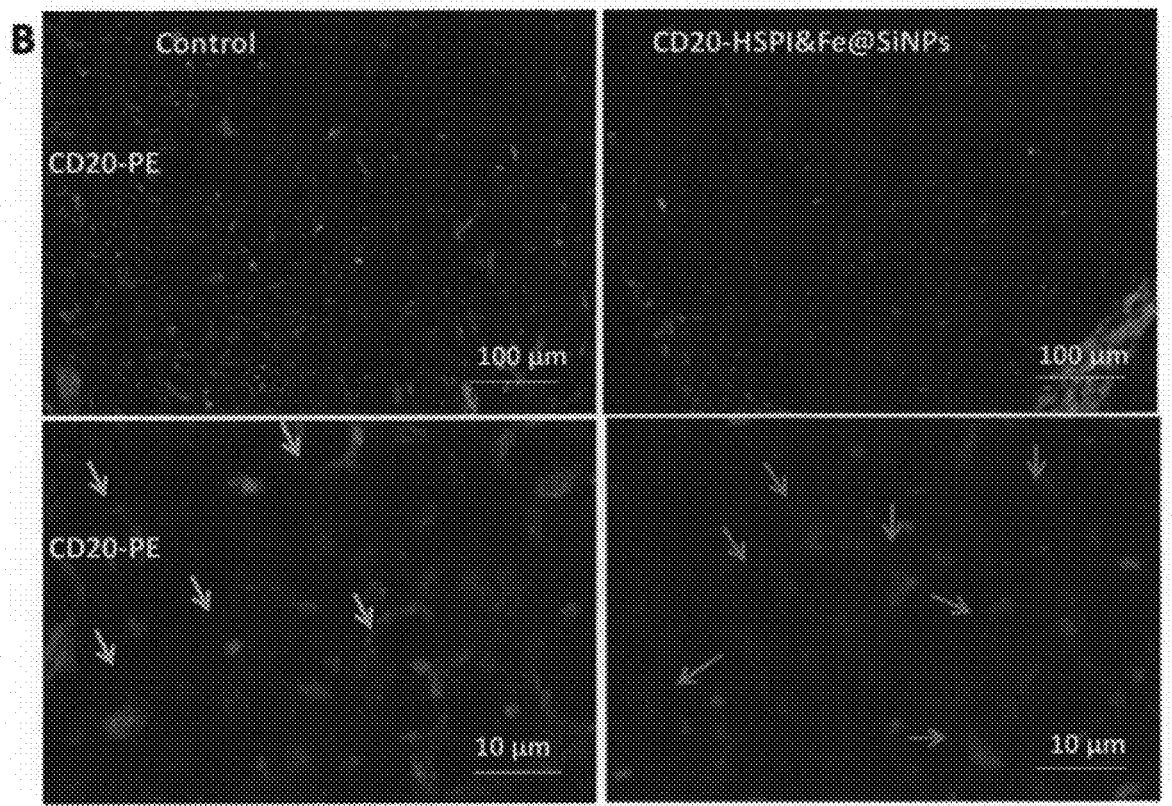
FIG. 7B are images showing IHC staining for CD20 on xenografts showing a complete ablation of LCSC by treatment of CD20-HSPI&Fe$_3$O$_4$@SiNPs.
Figures 7C, 7D, 7E:
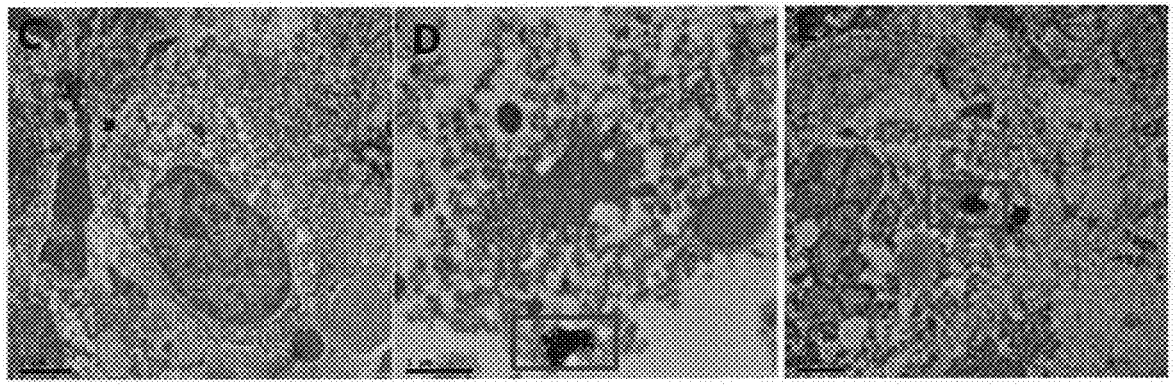
FIG. 7C and FIGS. 7D-7F are TEM images of tumor tissue in mice treated with i) PBS and ii) CD20-HSPI&Fe$_3$O$_4$@SiNPs (D-F) by retro-orbital sinus injection, respectively.
Figure 7F:
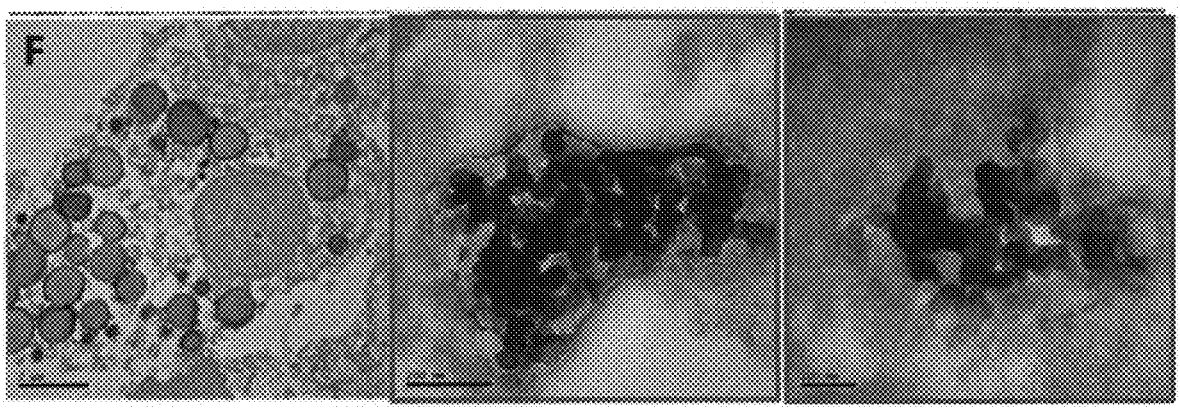

To further evaluate the anti-cancer efficiency by multifunctional NPs, ex vivo histology studies of the tumor tissue were performed. The tumor tissue of the control group was found relatively well maintained with cancer nests. However, significant necrosis occurred in the NPs-treated tumor region. The necrosis cells appeared as a round with dark eosinophilic cytoplasm and dense purple nucleus (FIG. 7A). To better determine the therapeutic efficacy of CD20-HSPI&$Fe_3O_4$@SiNPs, tumor specimens (after 36 days AMF treatment) were immune-histo-chemically stained with PE-conjugated CD20 antibodies. Treatment of tumors with CD20-HSPI&$Fe_3O_4$@SiNPs depleted LCSCs, as shown by a significant decrease in the expression of CD20, as compared to untreated tumors (FIG. 7B). Additionally, accumulation of nanoparticles was observed in the tumor tissues by using TEM imaging, indicating the targeting-tumor capacity of the multifunctional nanoparticle (FIGS. 7C-F). FIGS. 7C-7E show nanoparticles accumulated in the tumor tissue, which was seriously damaged after 36 days AMF treatment.

No Signs of Multifunctional NPs Induced Toxicity In Vivo

Figure 8:
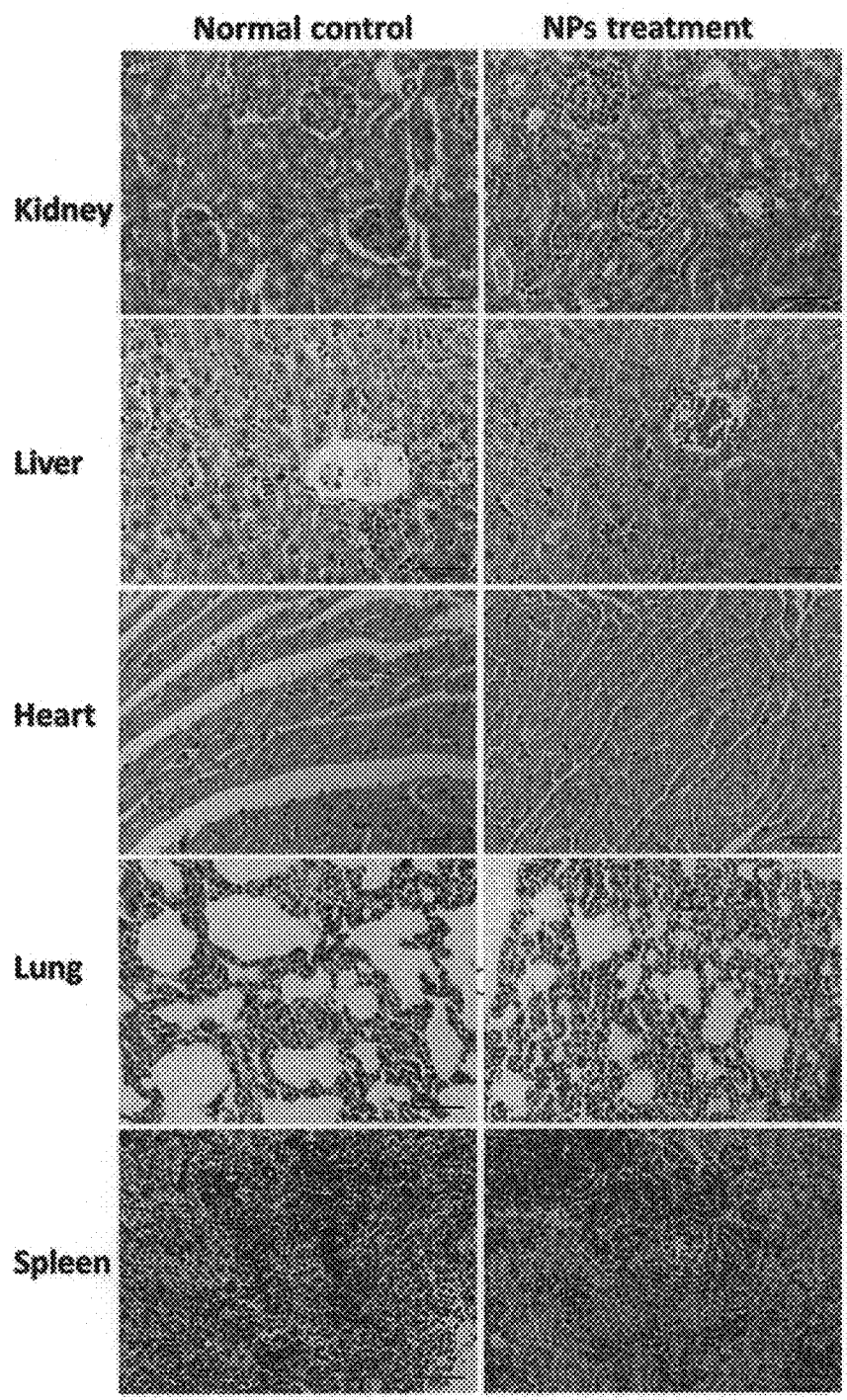
FIG. 8 are histological images of different organs in nude mouse.

In vivo toxicity of the multifunctional NPs was constantly studied after 36 days AMF treatment. The histopathologic effect of nanoparticles on the various organs such as heart, lung, liver and kidney were investigated. As shown in FIG. 8, no histopathologic changes were observed in treated groups compared with normal group as a control. Furthermore, there were no NPs accumulated in the tissues. From histopathological analysis, it could be confirmed that CD20-HSPI&$Fe_3O_4$@SiNPs did not seriously damage the organs. FIG. 8 reveals no signs of multifunctional NPs induced toxicity after 36 days. No anomalies were observed in the organs. The images were taken at 20× magnification.

Figure 9A:
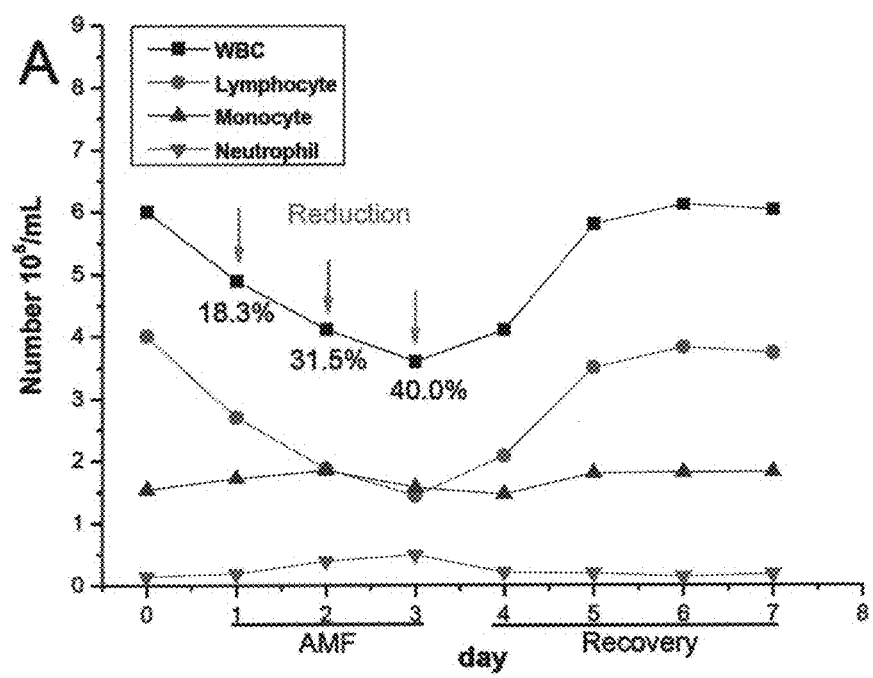
FIGS. 9A, 9B, 9C and 9D are graphs showing i) WBC counts and ii) B-cell changes in mice after CD20-HSPI&Fe$_3$O$_4$@SiNP-mediated AMF treatment, iii) percentage of WBC and B-cells in mice with CD20-HSPI&Fe$_3$O$_4$@SiNPs after 7 days recovery, iv) percentage of WBC and B-cells in mice without'CD20-HSPI&Fe$_3$O$_4$@SiNPs after 7 days recovery, and iv) CD20-HSPI&Fe$_3$O$_4$@SiNPs uptake in blood cells of mouse.
Figure 9B:
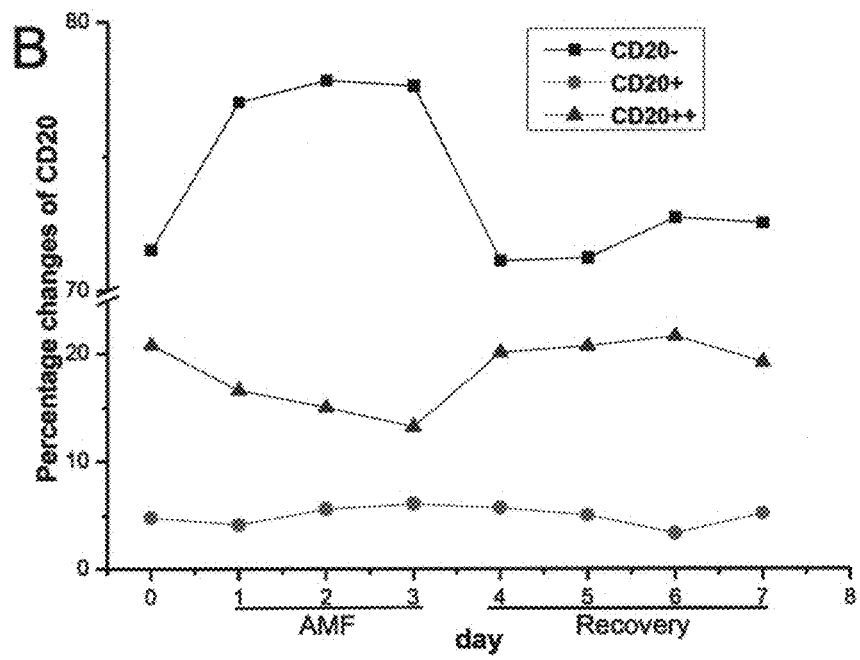
Figure 9C:
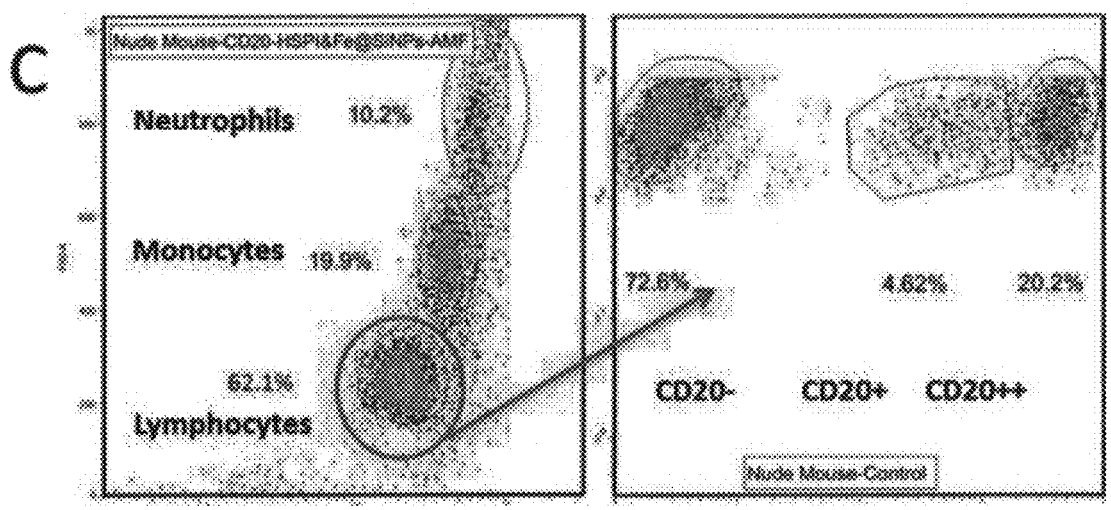
Figure 9D:
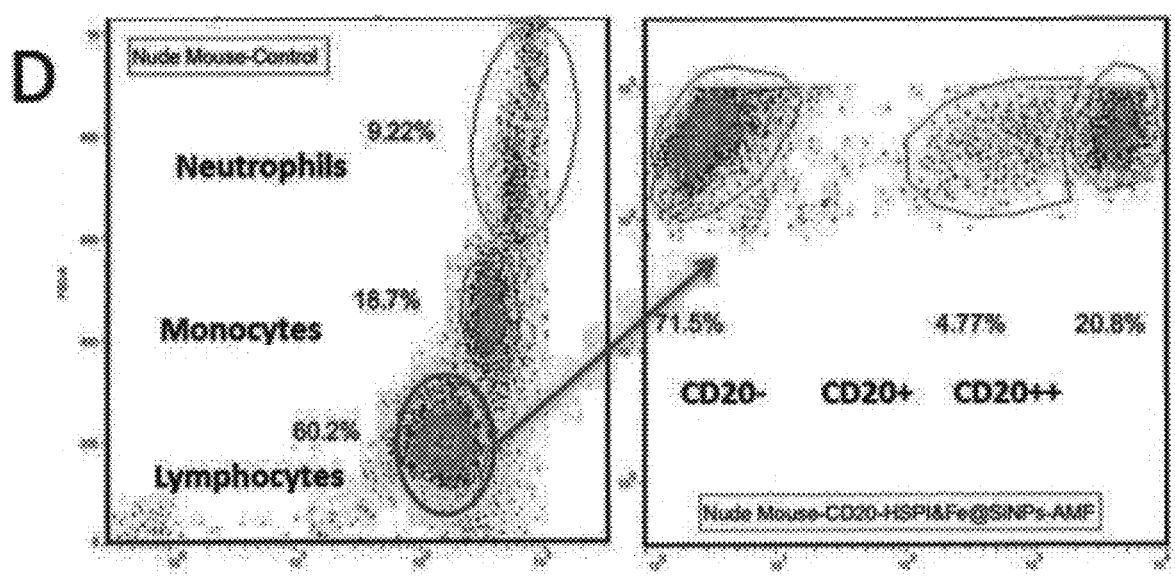
Figure 9E:
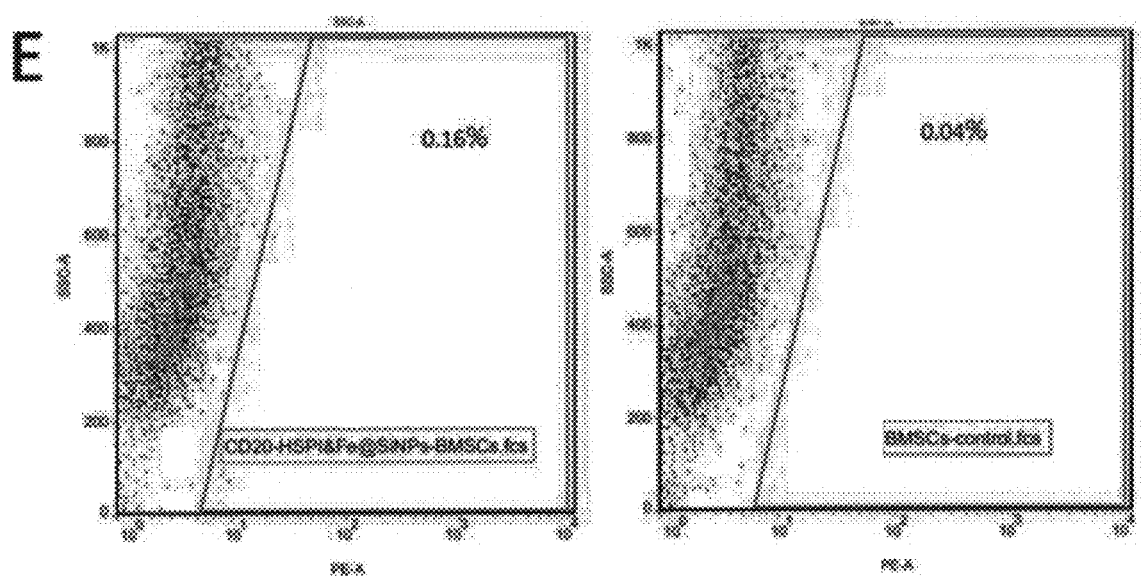
FIG. 9E shows CD20-HSPI&Fe$_3$O$_4$@SiNPs uptake in mouse MSCs monitored in the bone marrow by flow cytometry.

Immune cell injury and recovery induced by CD20-HSPI&$Fe_3O_4$@SiNPs treatment were assessed according to white blood cell (WBC) counts, including lymphocytes, monocytes, and neutrophils (FIG. 9A-D). Lymphocytes in WBC reduced significantly after 3 days AMF treatment and the number returned to the normal level by day 6 (FIG. 9A). In addition, the detailed analysis of B-cell was performed by using the CD20 antibody. Although, the B-cells nadir on day 3 was significantly reduced by treatment with CD20-HSPI&$Fe_3O_4$@SiNPs, a fast recovery of B-cells counts after day 4 was observed and returned to basal levels as early as day 6 (FIG. 9B). It is noteworthy that the number of B-cells begins to increase at approximate day 4 and the recovery of WBCs exhibited at day 6. The results suggest that damaged B-cells begin to recovery at approximately day 4 after AMF treatment by activation of hematopoietic function. Importantly, no CD20-HSPI@$Fe_3O_4$@SiNPs uptake was observed in MSCs from bone marrow of CD20-HSPI@$Fe_3O_4$@SiNPs treated mice (FIG. 9E). FIG. 9A shows WBC counts and FIG. 9B shows B-cell changes in mice after CD20-HSPI&$Fe_3O_4$@SiNP-mediated AMF treatment. FIG. 9C and FIG. 9D show percentage of WBCs and B-cells in mice with or without CD20-HSPI&$Fe_3O_4$@SiNPs after 7 days recovery; FIG. 9E shows CD20-HSPI&$Fe_3O_4$@SiNPs uptake in mouse MSCs monitored in the bone marrow by flow cytometry.

Figure 11:
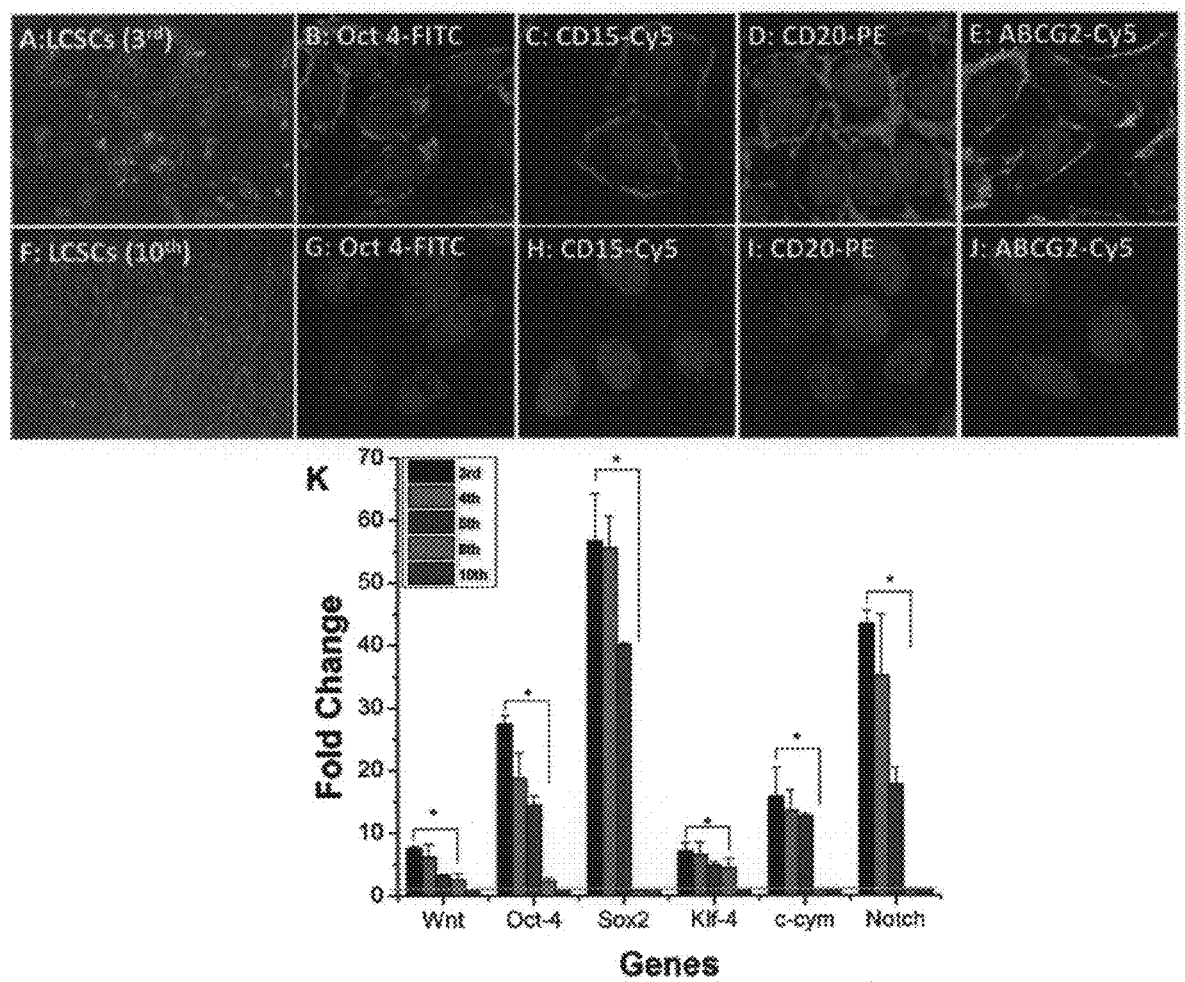
FIG. 11 illustrates morphology of $3^{rd}$ generation LCSCs (portion A in FIG. 11) and $10^{th}$ generation LCSCs (portion F in FIG. 11); immunofluorescence detection of stemness markers expression in $3^{rd}$ generation LCSCs (portions B-E in FIG. 11) and $10^{th}$ generation LCSCs (portions G-J in FIG. 11), scale bar=25 μm; and quantitative RT-PCR analysis of stemness genes expression in LCSCs with different generations (graph in portion K in FIG. 11) (data are mean±SD, *p<0.05 and **p<0.01 indicate significant difference, n=3)
Figure 12:
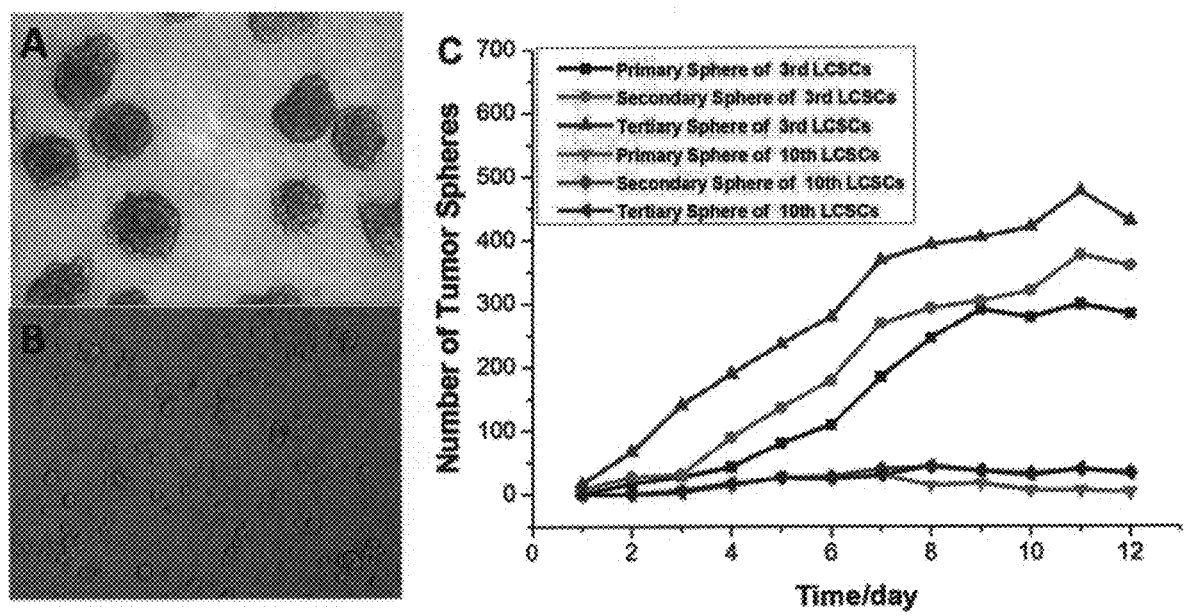
FIG. 12 includes images of primary tumor sphere formation by the $3^{rd}$ generation LCSCs (portion A in FIG. 12) and $10^{th}$ generation LCSCs (portion B in FIG. 12), and a graph showing time course of sequential primary, secondary, and tertiary tumor sphere formation, n=3 (portion C in FIG. 12).
Figure 13:
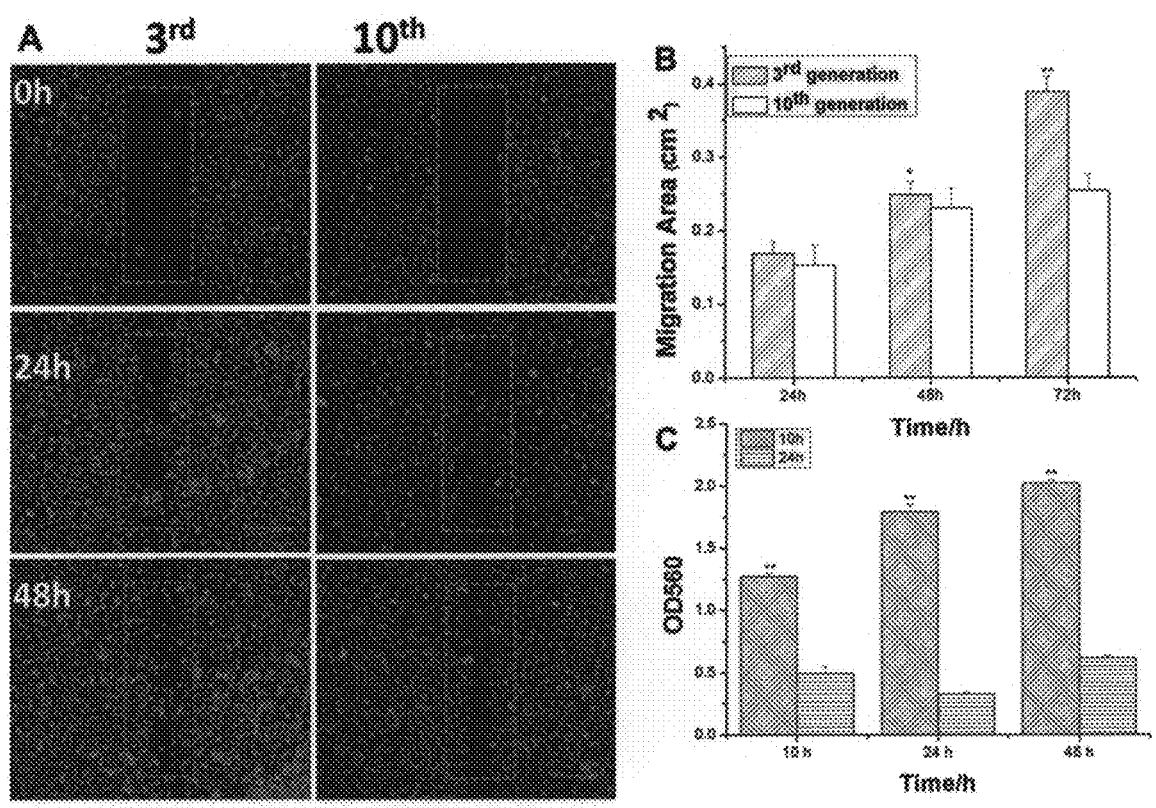
FIG. 13 illustrates migration in LCSCs evaluated using wound healing assays, and includes images from the same area captured at time 0, 24, and 48 h after wounding 9 portion A of FIG. 13); and graphs showing migratory and invasive capacities of LCSCs assessed by wound healing assay (portion B in FIG. 13) and matrigel transwell invasion assay (portion C in FIG. 13) (data represent the mean±SD, *p<0.05 and **p<0.01 indicate significant difference, n=3)
Figure 14:
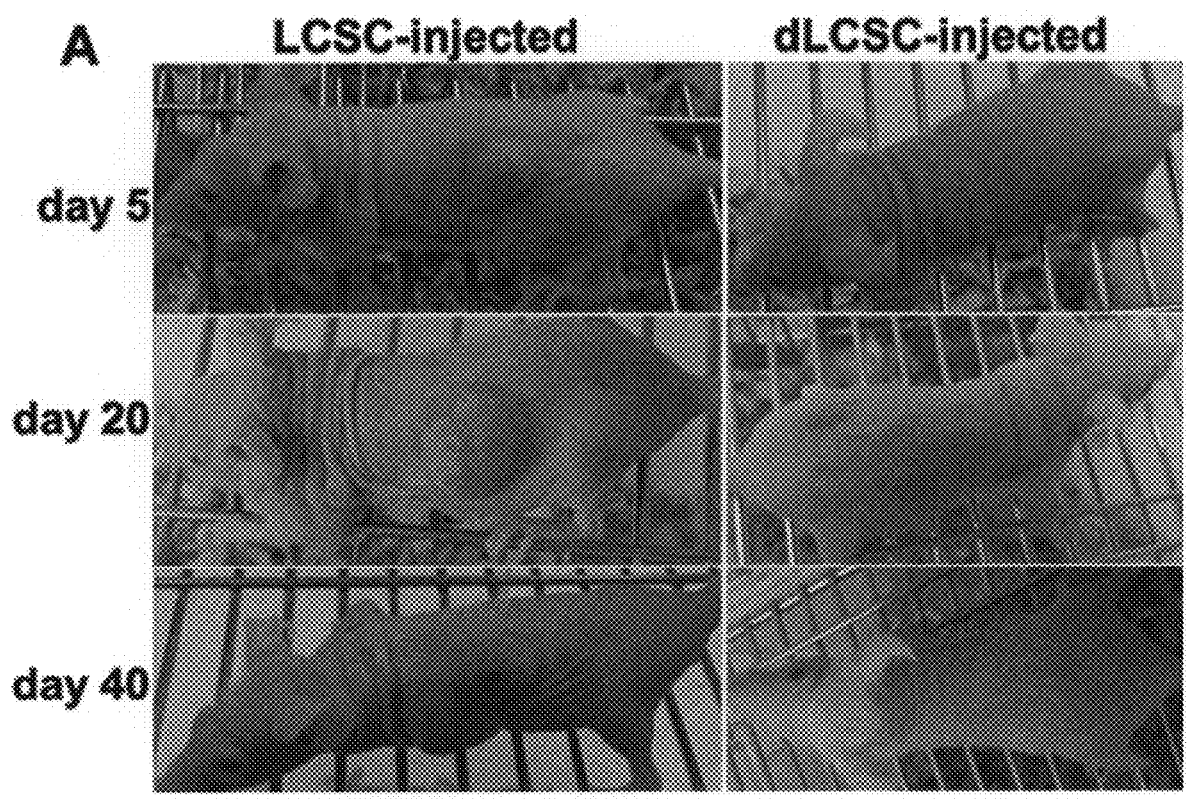
FIG. 14 illustrates in vivo tumorigenicity of LCSCs and dLCSCs in which portion A in FIG. 14 are representative images of xenograft tumors formed after subcutaneous injection with 1×10$^4$ LCSCs and dLCSCs, separately; and portion B in FIG. 13 shows tumor volume of LCSC and dLCSC xenograft-bearing nude mice (n=3) (data represents the mean±SD).

The intra-tumoral heterogeneity represents a major obstacle to the development of effective cancer treatment. A growing body of evidence suggests that tumors may be driven by a small population of transformed stem-like cells, called cancer stem cell, which have the ability to undergo both self-renewal, resistance to conventional therapy, and differentiation into the diverse cancer cell population that constitutes the bulk of the tumor. Recent identification of putative CSCs led to a quest for efficiency cancer therapies. However, while there is no current consensus on the optimal markers for CSCs, numerous studies employ surface antigens as markers for CSCs. In this invention, lung cancer stem cells (LCSCs) were isolated from the parental population of human lung tumor cells and characterized by surface markers and stemness markers, for example, CD20, CD15, ABCG2, and Oct4. Please see FIG. 11. These cells were examined to have the stronger capacities of tumor sphere formation, migration, and invasion than CD20-negative cells. Please see FIG. 12 and FIG. 13. In vivo tumorigenic study showed that the tumor formation of LCSCs was faster and resulted in increased tumor take compared with that observed after injection of differentiated LCSCs at the same cell number, indicating the high tumor-initiating capacity of LCSC. Please see FIG. 14. As these cells are highly tumorigenic, we hypothesized that efficiently eliminating LCSCs during conventional therapy may hold the key to successful treatments for lung cancer. Therefore, development of CSC-targeted therapy offers a promising therapeutic approach for complete elimination of cancer cells in order to achieve significantly better outcome for lung cancer patients.

Clinical results have suggested that nanoparticle-based drug delivery system can show enhanced efficacy in cancer therapy, while simultaneously reducing side-effects, as a result of properties including targeted localization in tumors and active cellular uptake, but cancer therapy towards CSCs by nanoparticle-based simultaneous thermotherapy and chemotherapy is unfortunately poorly investigated. In this study, we synthesized and characterized the biocompatible multifunctional silica-based nanoparticles encapsulated with magnetic cores ($Fe_3O_4$ NPs) and chemotherapeutic agents (including heat-shock protein inhibitors) and coated with specific antibody (CD20) against surface markers of lung cancer stem cells for targeted and combined thermotherapy and chemotherapy under an alternating magnetic field (AMF). To ascertain the magnetic and heat generation properties of CD20-$Fe_3O_4$@SiNPs, the saturation value of magnetization was tested and a hysteresis curve was plotted. The curve passed through the origin indicated that both $Fe_3O_4$ NPs and CD20-$Fe_3O_4$@SiNPs were super-paramagnetic. The heat generation property of the CD20-$Fe_3O_4$@SiNPs in an AMF was also evaluated. As shown in FIG. 2C, the NPs have an AMF-induced heating ability and generate heat in an AMF because of magnetic hysteresis. Next, the corresponding drug release in response to AMF was demonstrated. The NPs complex enabled prolonged HSPI retention compared to bare HSPI in vitro.

Although there have been proposal for hyperthermic cancer cell therapy, they relate to targeting cancer cells but not cancer stem cells (CSCs), resulting the relapse of tumor. Moreover, the overexpression of heat shock proteins in cancer cells trigger a defense mechanism, which provides protection from subsequent and more severe temperature. In this regard, in an embodiment heat shock protein inhibitors (using 17-Dimethylaminoethylamino-17-demethoxygeldanamycin (17-DMAG) as an example which targets HSP90 pathways under FDA-sanctioned clinical trials) was encapsulated in the magnetic nanoparticles as chemotherapeutic agents for simultaneous thermotherapy and chemotherapy. Additionally, the multifunctional NPs can be targeted delivered to LCSC by modifying with CD20 antibody. The ability to target LCSCs using the CD20-HSPI&$Fe_3O_4$@SiNPs was further confirmed in vivo using xenograft mouse tumor model. In vitro cellular uptake demonstrated that conjugation with CD20 antibody facilitated the targeting to LCSCs rather than non-modification NPs after 1 h incubation. However, the Fe$_3$O$_4$@SiNPs uptake rate by LCSCs slightly increased when the incubation time increased, indicating that a long incubation time could enhance non-specific uptake and reduce the difference between targeted and non-targeted nanoparticles, which was in good agreement with other studies. The in vitro selective targeting effect of CD20-Fe$_3$O$_4$@SiNPs to LCSCs was further evaluated by intracellular location study. It indicated that modification with the CD20 antibody could facilitate the internalization process, leading to more rapid distribution of nanoparticles throughout the cytoplasm. It was pointed out that receptor ubiquitination could trigger the clathrincoated pit scission from the membrane and complete the endocytic procedure. Preubiquitinated epidermal growth factor receptor (EGFR) and ErbB2 could be constitutively endocytosed into cells. Thus, the interaction between targeting molecules and receptors may induce the ubiquitination of receptors, leading to a rapid endocytosis of antibody-modified nanoparticles. The in vivo distribution data forcefully demonstrated that modification with the CD20 antibody could increase the tumor localization of nanoparticles within a short time, which was in agreement with many previous reports. To confirm the in vivo imaging results, various organs were excised for ex vivo imaging. Under the same excitation conditions as those used for whole animals, the fluorescence signals were clearly visible in the tumor of the mouse injected with CD20-Fe$_3$O$_4$@SiNPs, whereas weak signals were seen from the liver and no signal in the other organs. The kidney showed clear images, which may suggest that NPs were rapidly cleared from the body by the kidneys within 24 hours after injection of the NPs. To further appraise the potential side effects of these multifunctional nanoparticles on the blood compatibility, we carried out hemolysis and whole blood analysis. For hemolysis analysis, there was no visible hemoglobin was observed at the high concentration of 1 mg/mL, indicating that the multifunctional NPs had good hemocompatibility. After intravenous CD20-HSPI&Fe$_3$O$_4$@SiNPs treatment, there did not appear to be any changes in lymphocytes, monocytes and macrophages, and neutrophils number compared with normal control. Furthermore, the data obtained also showed that the targeting observed was specific for CSCs and not a generalized binding to "stem cells". Uptake of the CD20-HSPI&Fe$_3$O$_4$@SiNP was not detected in MSCs obtained from bone marrow and blood. Thus, due to the CD20-targeting moiety on the NPs, the specificity of this systemically administered CD20-HSPI&Fe$_3$O$_4$@SiNPs should also prevent deleterious and potentially dangerous side effects resulting from nonspecific toxicity in normal stem cells. This LCSC specificity is a significant advantage of this nano-delivery system with respect to potential clinical application. Another significant advantage of this multifunctional NP is CD20-HSPI&Fe$_3$O$_4$@SiNP-mediated LCSC-targeting combined thermotherapy and chemotherapy.

Studies leading to the present invention shows that thermotherapy, or hyperthermia, plays an important role in a combinational therapy regime, a temperature of 40° C. to 50° C. generated from iron oxide nanoparticles in AMF is considered optimal for hyperthermia. During the course of the present invention, the thermotherapeutic effects of CD20-Fe$_3$O$_4$@SiNPs was evaluated in vitro. In addition to the expected LCSCs death, the AMF controlling CD20-Fe$_3$O$_4$@SiNPs-mediated thermotherapy has also induced unexpected biological responses, such as tumor-specific immune responses as a result of heat-shock proteins expression. These results suggest that hyperthermia was able to kill not only LCSCs exposed to heat treatment, but also normal cells at temperature of 40° C.-50° C. To achieve the aim of selectively eliminating LCSCs at lower temperature (37° C.), HSP90 inhibitor 17-DMAG was encapsulated in CD20-Fe$_3$O$_4$@SiNPs to inhibit the expression of HSP90 and overcome the thermo-resistance of LCSCs. Both thermostherapeutic and chemotherapeutic effects of CD20-HSPI&Fe$_3$O$_4$@SiNPs on the survival of LCSCs at 37° C. under AMF for 30 min was investigated. It is to be noted that, compared with the other groups, CD20-HSPI&Fe$_3$O$_4$@SiNPs specifically targeted to LCSCs and decreased the survival rate by AMF application. Furthermore, the apoptotic and necrotic analysis by flow cytometry confirmed that the multifunctional NPs kill LCSCs by causing critical membrane damage and consequent necrotic cell death. The temperature in LCSCs is increased to above 42° C., which caused critical membrane damage to cells and consequent necrotic cell death, indicating that necrosis was the predominant form of cell death observed in LCSCs after NPs-mediated AMF treatment. To confirm the hypothesize that tumor growth may be effectively inhibited in vivo by selectively targeting CSCs with a combination of AMF-induced thermal destruction and chemotherapeutic drugs utilizing the multiple functions of nanoparticles, the tumor-targeting efficacy of CD20-HSPI&Fe$_3$O$_4$@SiNPs was then evaluated in mice bearing tumors derived from human LCSCs. This study has disclosed not only tumor growth inhibition, but also complete tumor regression, in animal models of cancer after treatment with the combination of thermotherapy and chemotherapy. Such complete tumor responses likely reflect the elimination of LCSCs. The mouse was placed in a water-cooled magnetic induction coil and applied AMF for 30 min. For the untreated control group of mice, tumor size dramatically increased. However, for the group that received the thermos-therapeutic and chemotherapeutic treatment with CD20-HSPI&Fe$_3$O$_4$@SiNPs, the tumor growth was inhibited during the same period. The mice treated with HSPI&Fe$_3$O$_4$@SiNPs hyperthermia showed growth behaviors similar to the untreated control. The he tumor tissue subjected to hyperthermia treatment with CD20-HSPI&Fe$_3$O$_4$@SiNPs using H&E staining was analyzed. The temperature in tumor tissue significantly increased to above 45° C., which causes necrosis of cancer cells, but does not damage surrounding normal tissue. Furthermore, PE-conjugated CD20 IHC staining results showed no fluorescence signal in xenograft tumors with CD20-HSPI&Fe$_3$O$_4$@SiNPs treatment (FIG. 7B, right), confirming the LCSC-targeting reactivity and therapeutic efficacy of the CD20-HSPI&Fe$_3$O$_4$@SiNPs. Taken together, these results confirmed the LCSC-targeting ability as well as antitumor efficacy of the combined thermos-therapeutic and chemotherapeutic nano-delivery system.

In the course leading to the present invention, the postmortem histopathology of the heart, liver, lung, spleen, and kidney to study any potential changes in organ morphology in tumor bearing mice was analyzed. No obvious morphological difference was observed in the CD20-HSPI&Fe$_3$O$_4$@SiNPs groups compared to the tumor-bearing mice without treatment. To comprehensively understand the response of immune cells and bone marrow to NPs-mediated AMF treatment, especially in cells which constitute the hematopoietic niche, the peripheral blood and whole bone marrow (mainly composed of bone MSCs) were collected in order to identify the changes of WBCs, especially, B-cells. It has reported that CD20 is a B-cell specific differentiation antigen that is expressed on mature B cells but not on early B-cell progenitors or later mature plasma cells. It shows that the B-cells nadir on day 3 was significantly reduced by treatment with CD20-HSPI&Fe$_3$O$_4$@SiNPs, but new pre-B-cells were generated by differentiation of hematopoietic stem cells during recovery period. With this great versatility and flexibility of NP, proven safety, and CSC-targeting advantage, this nano-delivery system has the potential for clinical translation to become a platform for simultaneous thermotherapy and chemotherapy of cancers.

As demonstrated above, a multifunctional nanoparticle, composed of Fe$_3$O$_4$ nanoparticles and HSPI, simultaneously delivering both hyperthermia and chemotherapeutics agent to tumor region was developed.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose. In this regard, the skilled person will be aware of at least the reference listed below, and contents of all these references are incorporated in their entirety.

REFERENCES

1. Tannishtha Reya, Sean J. Morrison, Michael F. Clarke, Irving L. Weissman. Stem cells, cancer, and cancer stem cells. *Nature*, 2001, 414: 105-111.
2. Connie Eaves. Cancer stem cells: Here, there, everywhere? *Nature*, 2008, 456: 581-582.
3. Ke Chen, Yinghui Huang, Jilong Chen. Understanding and targeting cancer stem cells: therapeutic implications and challenges. *Acta Pharmacologica Sinica*, 2013, 34: 732-740.
4. Tushar J. Desai, Douglas G. Brownfield, Mark A. Krasnow. Alveolar progenitor and stem cells in lung development, renewal and cancer. *Nature*, 2014, 507: 190-194.
5. S Akunuru, Q James Zhai, Y Zheng. Non-small cell lung cancer stem/progenitor cells are enriched in multiple distinct phenotypic subpopulations and exhibit plasticity. *Cell Death and Disease*, 2012, 3: e352.
6. Z Zhang, Y Zhou, H Qian, G Shao, X Lu, Q Chen, X Sun, D Chen, R Yin, H Zhu, Q Shao, W Xu. Stemness and inducing differentiation of small cell lung cancer NCI-H446 cells, *Cell Death and Disease*, 2013, 4: e633.
7. Josep Domingo-Domenech, Samuel J. Vidal, Veronica Rodriguez-Bravo, Mireia Castillo-Martin, S. Aidan Quinn, Ruth Rodriguez-Barrueco, et al. Suppression of Acquired Docetaxel Resistance in Prostate Cancer through Depletion of Notch- and Hedgehog-Dependent Tumor-Initiating Cells. *Cancer Cell*, 2012; 22: 373-388.
8. Andrew R. Burke, Ravi N. Singh, David L. Carroll, Frank M. Torti, Suzy V. Torti. Targeting Cancer Stem Cells with Nanoparticle-Enabled Therapies. *J Mol Biomarkers Diagn*, 2012, S: 8.
9. Wang, Liu, Wu, Wu, and Yiming Wu. Involvement of ROS in the inhibitory effect of thermotherapy combined with chemotherapy on A549 human lung adenocarcinoma cell growth through the Akt pathway. *Oncology Reports*, 2012, 28: 1369-1375.
10. Shawn T Beug, Vera A Tang, Eric C LaCasse, Herman H Cheung, Caroline E Beauregard, Jan Brun, et al. Smac mimetics and innate immune stimuli synergize to promote tumor death. *Nature Biotechnology*, 2014, 32: 182-190.
11. Feifei Li, Changqi Zhao, Lili Wang. Molecular-targeted agents combination therapy for cancer: Developments and potentials. *International Journal of Cancer*, 2014, 134: 1257-1269.
12. Haiyan Chen, Xin Zhang, Shuhang Dai, Yuxiang Ma, Sisi Cui, Samuel Achilefu, Yueqing Gu. Multifunctional Gold Nanostar Conjugates for Tumor Imaging and Combined Photothermal and Chemo-therapy. *Theranostics*, 2013, 3: 633-649.
13. Shyh-Dar Li, Yun-Ching Chen, Michael J Hackett, Leaf Huang. Tumor-targeted Delivery of siRNA by Self-assembled Nanoparticles. *Molecular Therapy*, 2007, 16: 163-169.
14. Mark E. Davis, Zhuo (Georgia) Chen, Dong M. Shin. Nanoparticle therapeutics: an emerging treatment modality for cancer. *Nature Reviews Drug Discovery*, 2008, 7: 771-782.
15. Veronika Mamaeva, Jessica M Rosenholm, Laurel Tabe Bate-Eya, Lotta Bergman, Emilia Peuhul, Alain Duchanoy, et al. Mesoporous Silica Nanoparticles as Drug Delivery Systems for Targeted Inhibition of Notch Signaling in Cancer. *Molecular Therapy*, 2011, 19: 1538-1546.
16. Yong Wang, Shujun Gao, Wen-Hui Ye, Ho Sup Yoon, Yi-Yan Yang. Co-delivery of drugs and DNA from cationic core-shell nanoparticles self-assembled from a biodegradable copolymer. *Nature Materials*, 2006, 5: 791-796.
17. Xiyang Sun, Zhiqing Pang, Hongxing Ye, Bo Qiu, Liangran Guo, Jingwei Li, et al. Co-delivery of pEGFP-hTRAIL and paclitaxel to brain glioma mediated by an angiopep-conjugated liposome. *Biomaterials*, 2012, 33: 916-924.
18. Huan Meng, Wilson X. Mai, Haiyuan Zhang, Min Xue, Tian Xia, Sijie Lin, et al. Codelivery of an Optimal Drug/siRNA Combination Using Mesoporous Silica Nanoparticles To Overcome Drug Resistance in Breast Cancer in Vitro and in Vivo. *ACS Nano*, 2013, 7: 994-1005.
19. Dandan Liu, Changqing Yi, Kaiqun Wang, Chi-Chun Fong, Zuankai Wang, Pik Kwan Lo, et al. Reorganization of Cytoskeleton and Transient Activation of Ca2+ Channels in Mesenchymal Stem Cells Cultured on Silicon Nanowire Arrays. *ACS Applied Materials & Interfaces*, 2013, 5: 13295-13304.
20. Dandan Liu, Changqing Yi, Chi-Chun Fong, Qinghui Jin, Zuankai Wang, Wai-Kai Yu, et al. Activation of multiple signaling pathways during the differentiation of mesenchymal stem cells cultured in a silicon nanowire microenvironment. *Nanomedicine: Nanotechnology, Biology and Medicine*, 2014, 10: 1153-1163.
21. Jordan, C T. Cancer stem cells: controversial or just misunderstood? *Cell Stem Cell*, 2009, 4: 203-205.
22. Hiroaki Mamiya, Balachandran Jeyadevan. Hyperthermic effects of dissipative structures of magnetic nanoparticles in large alternating magnetic fields. *Scientific Reports*, 2001, 1: 157-163.
23. Kobayashi, T. Cancer hyperthermia using magnetic nanoparticles. *Biotechnology Journal*, 2011, 6: 1342-1347.
24. Paul Workman, Marissa V Powers. Chaperoning cell death: a critical dual role for Hsp90 in small-cell lung cancer. *Nature Chemical Biology*, 2007, 3: 455-457.
25. Huile Gao, Zhi Yang, Shuang Zhang, Shijie Cao, Shun Shen, Zhiqing Pang, Xinguo Jiang. Ligand modified 26. Mickler, F. M. et al. Tuning nanoparticle uptake: live-cell imaging reveals two distinct endocytosis mechanisms mediated by natural and artificial EGFR targeting ligand. *Nano Letter,* 2012, 12: 3417-3423.
27. Harvey T. McMahon, Emmanuel Boucrot. Molecular mechanism and physiological functions of clathrin-mediated endocytosis. *Nature Reviews Molecular Cell Biology,* 2011, 12: 517-533.
28. Tram Thu Vuonga, Christian Bergerb, Vibeke Bertelsena, Marianne Skeie Rødlanda, Espen Stangb, Inger Helene Madshus. Preubiquitinated chimeric ErbB2 is constitutively endocytosed and subsequently degraded in lysosomes. *Experimental Cell Research,* 2013, 319, 32-45.
29. Vibeke Bertelsen, Malgorzata Magdalena Sak, Kamilla Breen, Marianne S. Rodland, Lene E. Johannessen, Linton M. Traub, et al. A chimeric pre-ubiquitinated EGF receptor is constitutively endocytosed in a clathrin-dependent, but kinase-independent manner. *Traffic,* 2011, 12, 507-520.
30. Ralph Weissleder, Kimberly Kelly, Eric Yi Sun, Timur Shtatland, Lee Josephson. Cell-specific targeting of nanoparticles by multivalent attachment of small molecules. *Nature Biotechnology,* 2005, 23, 1418-1423.
31. Monty Liong, Jie Lu, Michael Kovochich, Tian Xia, Stefan G. Ruehm, Andre E. Nel, et al. Multifunctional Inorganic Nanoparticles for Imaging, Targeting, and Drug Delivery. *ACS Nano,* 2008, 2: 889-896.
32. Jae-Hyun Lee, Jung-tak Jang, Jin-sil Choi, Seung Ho Moon, Seung-hyun Noh, Ji-wook Kim, et al. Exchange-coupled magnetic nanoparticles for efficient heat induction. *Nature Nanotechnology,* 2011, 6: 418-422.
33. Thomas A. Davis, Debra K. Czerwinski, Ronald Levy. Therapy of B-Cell Lymphoma with Anti-CD20 Antibodies Can Result in the Loss of CD20 Antigen Expression. *Clinical Cancer Research,* 1999, 5: 611-615.

The invention claimed is:

1. A composition in the form of a nanoparticle with a diameter from 5 to 50 nanometers comprising:
   a central core portion including magnetic $Fe_3O_4$ nanoparticles adapted to act as a heat source when subjected to a magnetic field and a chemotherapeutic agent configured to treat cancer tissues,
   a shell portion including a shell member encapsulating said core portion, and
   antibodies configured to target cancer stem cells and adhered to surface of said shell member,
   wherein the chemotherapeutic agent includes a heat shock protein inhibitor and is releasable on activation of the heat source due to the magnetic field, and the shell member is made of silica or a silica based material,
   wherein surface of the nanoparticle is modified with the antibodies capable of binding with a cluster of differentiation molecules on the cell surface of the target cancer stem cells, whereby by way of combination of specificity of the nanoparticle composition due to the antibody, thermo-therapeutic effect of the $Fe_3O_4$ nanoparticles, and release of the heat shock protein inhibitor on site at the target cancer stem cells, inhibition of the target cancer stem cells is synergistically and additionally enhanced is increased; and
   wherein the heat shock protein inhibitor includes or is 17-(Dimethylaminoethylamino)-17-demethoxygeldanamycin (17-DMAG).

2. A nanoparticle composition as claimed in claim 1, further comprising fluorescent dyes attached to the antibodies for in vivo localization.

3. A composition as claimed in claim 2, wherein said antibodies are anti-CD 20 antibodies.

4. A composition as claimed in claim 1, wherein said magnetic nanoparticles are magnetically responsive, and comprise or are super-paramagnetic nanoparticles.

5. A composition as claimed in claim 1, wherein said magnetic nanoparticles are configured to be responsive to alternating magnetic field.

6. A composition as claimed in claim 1, wherein said antibodies are coated on outwardly facing surface of said shell member.

7. A method of treatment of cancer by way of targeting cancer stem cells, comprising administering a nanoparticle composition as claimed in claim 1, forming a complex of the nanoparticle composition and the target cancer stem cells, and exposing a target site in which the cancer cells reside to an energy source for effecting elevation of temperature of the magnetic nanoparticles, and release of the chemotherapeutic agent from the shell portion for destroying the cancer cells of the composition-cancer cell complex in the target site, wherein the energy source is an alternating magnetic field whereby extent of elevation of temperature and release of the chemotherapeutic agent is controllable by the alternating magnetic field.

8. A method as claimed in claim 7, comprising a step of elevating temperature of the target site to 40° C. to 52° C.

9. A method as claimed in claim 7, comprising a step of administering said nanoparticle composition intravenously, or at a dose of 10 mg to 500 mg of said nanoparticle composition intravenously per kg of body weight.

10. A method as claimed in claim 7, comprising said administration of the nanoparticle composition once a week.

* * * * *